United States Patent [19]

Prosser et al.

[11] Patent Number: 4,859,056
[45] Date of Patent: Aug. 22, 1989

[54] MULTIPLE-PULSE METHOD AND APPARATUS FOR USE IN OXIMETRY

[75] Inventors: Stephen J. Prosser, Lynnwood; Robert E. Smith, Edmonds, both of Wash.

[73] Assignee: Physio-Control Corporation, Redmond, Wash.

[21] Appl. No.: 897,661

[22] Filed: Aug. 18, 1986

[51] Int. Cl.$^4$ ............................................. G01N 33/48
[52] U.S. Cl. ..................................................... 356/41
[58] Field of Search .......................... 356/41; 128/633; 364/416

[56] References Cited

U.S. PATENT DOCUMENTS

| | | | |
|---|---|---|---|
| 2,706,927 | 4/1955 | Wood | 88/14 |
| 3,704,706 | 12/1972 | Herczfeld et al. | 128/2 |
| 3,847,483 | 11/1974 | Shaw et al. | 356/41 |
| 3,998,550 | 12/1976 | Konishi et al. | 356/39 |
| 4,086,915 | 5/1978 | Kofsky et al. | 128/2 |
| 4,114,604 | 9/1978 | Shaw et al. | 128/2 |
| 4,167,331 | 9/1979 | Nielsen | 356/39 |
| 4,266,554 | 5/1981 | Hamaguri | 128/633 |
| 4,357,105 | 11/1982 | Loretz | 356/40 |
| 4,407,290 | 10/1983 | Wilber | 128/633 |
| 4,446,871 | 5/1984 | Imura | 356/41 |
| 4,523,279 | 6/1985 | Sperinde et al. | 356/41 |
| 4,621,643 | 11/1986 | New et al. | 128/633 |

FOREIGN PATENT DOCUMENTS 0102816 3/1984 European Pat. Off. .
104772 4/1984 European Pat. Off. .

Primary Examiner—Bruce C. Anderson
Attorney, Agent, or Firm—Christensen, O'Connor, Johnson & Kindness

[57] ABSTRACT

The disclosed invention is for use in extracting more accurate information from signals employed in pulse oximetry. Basically, pulse oximetry involves the illumination of arterial blood flowing in tissue with light at two wavelengths. Upon emerging from the tissue the light is received by a detector (38) that produces signals that are proportional to the intensity of the light received at each of the wavelengths. Each signal includes a slowly varying baseline component representing the attenuation $\beta(t)$ of light produced by bone, tissue, skin, and hair. The signals also include pulsatile components representing the attenuation $\alpha(t)$ produced by the changing blood volume and oxygen saturation within the finger. The signals produced by the detector (38) are converted by an analog-to-digital (A/D) converter (72) for subsequent analysis by a microcomputer (16). The microcomputer (16) extracts the following information from the signal corresponding to each wavelength. $V_H$ is determined to be the signal magnitude at a second pulse diastole. $V_L$ is, similarly, the signal magnitude at systole of the same pulse. A term $\Delta V$ is identified equal in value to the difference in signal magnitudes at the adjacent systoles. Finally, values are determined for $\Delta ts$ and $\Delta tp$, being the interval between an adjacent systole and diastole and the pulse period, respectively. The microcomputer (16) then determines a value for $R_{OS}$ in accordance with the relationship:

$$R_{OS} = \frac{\ln\left[\dfrac{V_H}{V_L - (\Delta ts \Delta V / \Delta tp)}\right] @ \lambda_1}{\ln\left[\dfrac{V_H}{V_L - (\Delta ts \Delta V / \Delta tp)}\right] @ \lambda_2}$$

Empirically derived oxygen saturation curves are used to develop an indication of the oxygen saturation from the value of $R_{OS}$ computed.

29 Claims, 8 Drawing Sheets

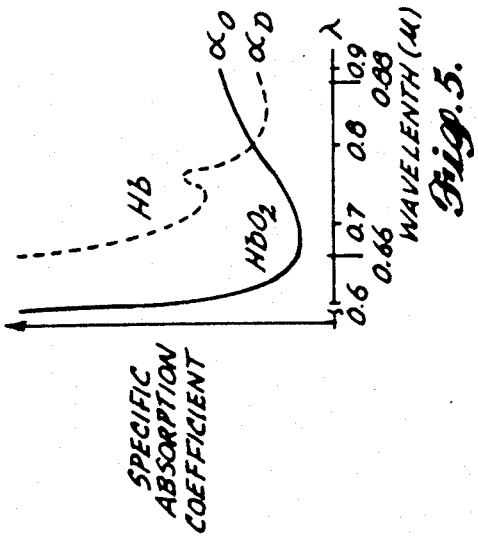
Fig. 5.
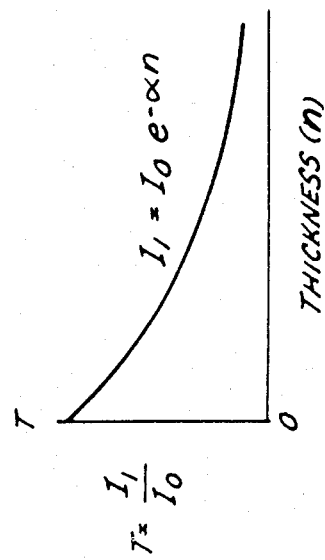
Fig. 4.
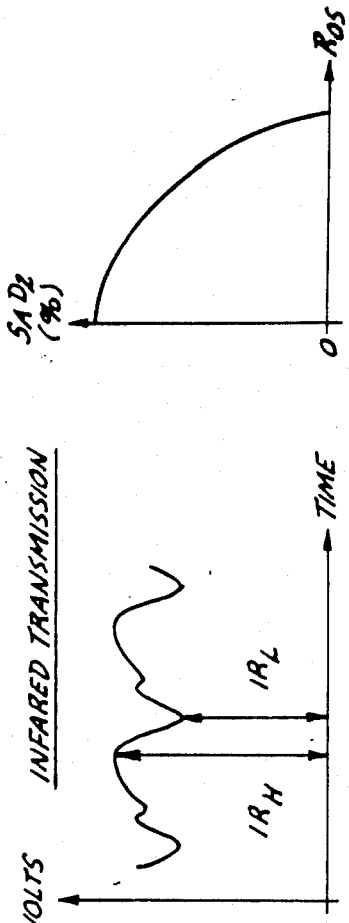
Fig. 7.
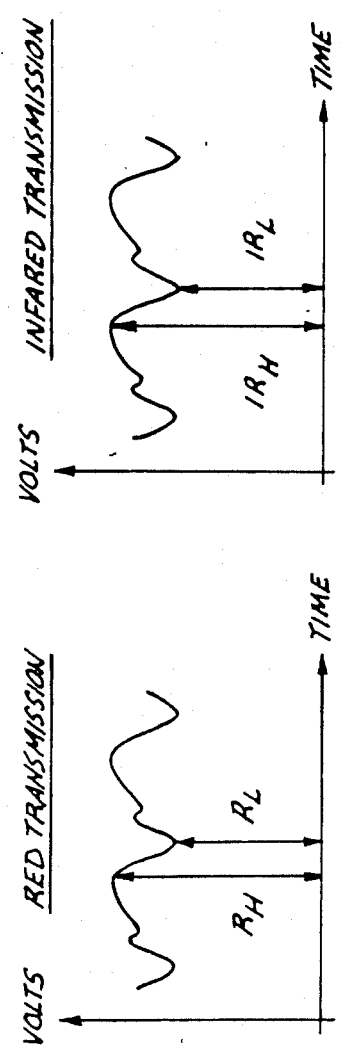
Fig. 11.
Fig. 10.

MULTIPLE-PULSE METHOD AND APPARATUS FOR USE IN OXIMETRY

BACKGROUND OF THE INVENTION

This invention relates to oximetry and, more particularly, to information extraction techniques developed for pulse oximetry.

The arterial oxygen saturation and pulse rate of an individual may be of interest for a variety of reasons. For example, in the operating room up-to-date information regarding oxygen saturation can be used to signal changing physiological factors, the malfunction of anaesthesia equipment, or physician error. Similarly, in the intensive care unit, oxygen saturation information can be used to confirm the provision of proper patient ventilation and allow the patient to be withdrawn from a ventilator at an optimal rate.

In many applications, particularly including the operating room and intensive care unit, continual information regarding pulse rate and oxygen saturation is important if the presence of harmful physiological conditions is to be detected before a substantial risk to the patient is presented. A noninvasive technique is also desirable in many applications, for example, when a home health care nurse is performing a routine checkup, because it increases both operator convenience and patient comfort. Pulse transmittance oximetry is addressed to these problems and provides noninvasive, continual information about pulse rate and oxygen saturation. The information produces, however, is only useful when the operator can depend on its accuracy. The method and apparatus of the present invention are, therefore, directed to the improved accuracy of such information without undue cost.

As will be discussed in greater detail below, pulse transmittance oximetry basically involves measurement of the effect arterial blood in tissue has on the intensity of light passing therethrough. More particularly, the volume of blood in the tissue is a function of the arterial pulse, with a greater volume present at systole and a lesser volume present at diastole. Because blood absorbs some of the light passing through the tissue, the intensity of the light emerging from the tissue is inversely proportional to the volume of blood in the tissue. Thus, the emergent light intensity will vary with the arterial pulse and can be used to indicate a patient's pulse rate. In addition, the absorption coefficient of oxyhemoglobin (hemoglobin combined with oxygen in the blood, $HbO_2$) is different from that of deoxygenated hemoglobin (Hb) for most wavelengths of light. For that reason, differences in the amount of light absorbed by the blood at two different wavelengths can be used to indicate the hemoglobin oxygen saturation, % $SaO_2$ (OS), which equals $([HbO_2]/([Hb]+[HbO_2]))\times 100\%$. Thus, measurement of the amount of light transmitted through, for example, a finger can be used to determine both the patient's pulse rate and hemoglobin oxygen saturation.

As will be appreciated, the intensity of light transmitted through a finger is a function of the absorption coefficient of both "fixed" components, such as bone, tissue, skin, and hair, as well as "variable" components, such as the volume of blood in the tissue. The intensity of light transmitted through the tissue, when expressed as a function of time, is often said to include a DC component, representing the effect of the fixed components on the light, and an AC pulsatile component, representing the effect that changing tissue blood volume has on the light. Because the attenuation produced by the fixed tissue components does not contain information about pulse and arterial oxygen saturation, the pulsatile signal is of primary interest. In that regard, many of the prior art transmittance oximetry techniques eliminate the DC component from the signal analyzed.

For example, in U.S. Pat. No. 2,706,927 (Wood) measurements of light absorption at two wavelengths are taken under a "bloodless" condition and a "normal" condition. In the bloodless condition, as much blood as possible is squeezed from the tissue being analyzed. Then, light at both wavelengths is transmitted through the tissue and absorption measurements made. These measurements indicate the effect that all nonblood tissue components have on the light. When normal blood flow has been restored to the tissue, a second set of measurements is made that indicates the influence of both the blood and nonblood components. The difference in light absorption between the two conditions is then used to determine the average oxygen saturation of the tissue, including the effects of both arterial and venous blood. As will be readily apparent, this process basically eliminates the DC, nonblood component from the signal that the oxygen saturation is extracted from.

For a number of reasons, however, the Wood method fails to provide the necessary accuracy. For example, a true bloodless condition is not practical to obtain. In addition, efforts to obtain a bloodless condition, such as by squeezing the tissue, may result in a different light transmission path for the two conditions. In addition to problems with accuracy, the Wood approach is both inconvenient and time consuming.

A more refined approach to pulse transmittance oximetry is disclosed in U.S. Pat. No. 4,086,915 (Kofsky et al.). The Kofsky et al. reference is of interest for two reasons. First, the technique employed automatically eliminates the effect that fixed components in the tissue have on the light transmitted therethrough, avoiding the need to produce bloodless tissue. More particularly, as developed in the Kofsky et al. reference from the Beer-Lambert law of absorption, the derivatives of the intensity of the light transmitted through the tissue at two different wavelengths, when multiplied by predetermined pseudocoefficients, can be used to determine oxygen saturation. Basic mathematics indicate that such derivatives are substantially independent of the DC component of the intensity. The pseudocoefficients are determined through measurements taken during a calibration procedure in which a patient first respires air having a normal oxygen content and, later, respires air of a reduced oxygen content. As will be appreciated, this calibration process is at best cumbersome.

The second feature of the Kofsky et al. arrangement that is of interest is its removal of the DC component of the signal prior to being amplified for subsequent processing. More particularly, the signal is amplified to allow its slope (i.e., the derivative) to be more accurately determined. To avoid amplifier saturation, a portion of the relatively large DC component of the signal is removed prior to amplification. To accomplish this removal, the signal from the light detector is applied to the two inputs of a differential amplifier as follows. The signal is directly input to the positive terminal of the amplifier. The signal is also passed through a low-resolution A/D converter, followed by a D/A converter, before being input to the negative terminal of the amplifier. The A/D converter has a resolution of approximately 1/10 that of the input signal. For example, if the signal is at 6.3 volts, the output of the A/D converter would be 6 volts. Therefore, the output of the converter represents a substantial portion of the signal, which typically can be used to approximate the DC signal level. Combination of that signal with the directly applied detector signal at the amplifier produces an output that can be used to approximate the AC signal. As will be readily appreciated, however, the process may be relatively inaccurate because the output of the A/D converter is often a poor indicator of the DC signal.

U.S. Pat. No. 4,167,331 (Nielson) discloses another pulse transmittance oximeter. The disclosed oximeter is based upon the principle that the absorption of light by a material is directly proportional to the logarithm of the light intensity after having been attenuated by the absorber, as derived from the Beer-Lambert law. The oximeter employs light-emitting diodes (LEDs) to produce light at red and infrared wavelengths for transmission through tissue. A photosensitive device responds to the light produced by the LEDs and attenuated by the tissue, producing an output current. That output current is amplified by a logarithmic amplifier to produce a signal having AC and DC components and containing information about the intensity of light transmitted at both wavelengths. Sample-and-hold circuits demodulate the red and infrared wavelength signals. The DC components of each signal are then blocked by a series bandpass amplifier and capacitors, eliminating the effect of the fixed absorptive components from the signal. The resultant AC signal components are unaffected by fixed absorption components, such as hair, bone, tissue, skin. An average value of each AC signal is then produced. The ratio of the two averages is then used to determine the oxygen saturation from empirically determined values associated with the ratio. The AC components are also used to determine the pulse rate.

Another reference addressed to pulse transmittance oximetry is U.S. Pat. No. 4,407,290 (Wilber). In that refernce, light pulses produced by LEDs at two different wavelengths are applied to, for example, an earlobe. A sensor responds to the light transmitted through the earlobe, producing a signal for each wavelength having a DC and AC component resulting from the presence of constant and pulsatile absorptive components in the earlobe. A normalization circuit employs feedback tos cale both signals so that the DC nonpulsatile components of each are equal and the offset voltages removed. Decoders separate the two signals, so controlled, into channels A and B where the DC component is removed from each. The remaining AC components of the signals are amplified and combined at a multiplexer pror to analog-to-digital (A/D) conversion. Oxygen saturation is determined by a digital processor in accordance with the following relationship:

$$OS = \frac{X_1 R(\lambda_1) + X_2 R(\lambda_2)}{X_3 R(\lambda_1) + X_4 R(\lambda_2)}$$

wherein empirically derived data for the constants $X_1$, $X_2$, $X_3$ and $X_4$ is stored in the processor.

European patent application No. 83304939.8 (New, Jr. et al.) discloses an additional pulse transmittance oximeter. Two LEDs expose a body member, for example, a finger, to light having red and infrared wavelengths, with each LED having a one-in-four duty cycle. A detector produces a signal in response that is then split into two channels. The one-in-four duty cycle allows negatively amplified noise signals to be integrated with positively amplified signals, including the detector response and noise, thereby eliminating the effect of noise on the signal produced. The resultant signals include a substantially constant DC component and a pulsatile AC component. To improve the accuracy of a subsequent analog-to-digital (A/D) conversion, a fixed DC value is subtracted from the signal prior to the conversion. This level is then added back in by a microprocessor after the conversion. Logarithmic analysis is avoided by the microprocessor in the following manner. For each wavelength of light transmitted through the finger, a quotient of the pulsatile component over the constant component is determined. The ratio of the two quotients is then determined and fitted to a curve of independently derived oxygen saturations. To compensate for the different transmission characteristics of different patients' fingers, an adjustable drive source for the LEDs is provided. In addition, an apparatus for automatically calibrating the device is disclosed.

The prior art of oximetry has, however, failed to produce the type of highly accurate, quickly repsonsive information needed to ensure user confidence in the equipment. This is particularly important in, for example, the operating room, where the availability of fast, relible information about oxygen saturation may determine the success of the operation. The disclosed invention addresses this problem and produces an accuracy previously unattainable by oximeters.

SUMMARY OF THE INVENTION

The present invention discloses a method of determining the oxygen saturation of arterial blood flowing in tissue that is illuminated with light at two wavelengths, the light being received upon emergence from the tissue by a detector that produces signals that are proportional to the intensity of the light received at each of the wavelengths. The method includes the steps of storing the magnitude of the signals at a plurality of sample times spaced over an interval greater than the period of one pulse and producing a single indication of the oxygen saturation of the arterial blood from the sample times and the magnitudes of the signals stored at the sample times.

In accordance with particular aspects of the invention, the sample times and magnitudes of the signals stored at the sample times may be processed in accordance with the relationships including:

$$R_{OS} = \frac{\ln(T_1/T_0) - m\ln(T_3/T_1) \ @ \ \lambda_1}{\ln(T_1/T_0) - m\ln(T_3/T_1) \ @ \ \lambda_2}$$

where:
$R_{OS}$ = the single indication of the oxygen saturation;
$\lambda_1$ = the first of the two wavelengths of the transilluminating light;
$\lambda_2$ = the second of the two wavelengths of the transilluminating light;
$T_0$ = the magnitude of the signal at the diastole of a first pulse exhibited by the arterial blood, for the wavelength indicated;
$T_1$ = the magnitude of the signal at the systole of the first pulse, for the wavelength indicated;
$T_3$ = the magnitude of the signal at the systole of a second pulse, for the wavelength indicated; and m = the ratio of the time between an adjacent diastole and systole to the time between adjacent diastoles.

$$R_{OS} = \frac{\ln\left[\frac{V_H}{V_L - (\Delta ts \Delta V / \Delta tp)}\right] @ \lambda_1}{\ln\left[\frac{V_H}{V_L - (\Delta ts \Delta V / \Delta tp)}\right] @ \lambda_2}$$

where:
$R_{OS}$ = the single indication of the oxygen saturation;
$\lambda_1$ = the first of the two wavelengths of the transilluminating light;
$\lambda_2$ = the second of the two wavelengths of the transilluminating light;
$V_H$ = the magnitude of the signal at the diastole of a second pulse exhibited by the arterial blood, for the wavelength indicated;
$V_L$ = the magnitude of the signal at the systole of the second pulse, for the wavelength indicated;
$\Delta V$ = the difference in the magnitude of the signal between the systole of the second pulse and the systole of a first pulse, for the wavelength indicated;
$\Delta ts$ = the difference in time between the systole and diastole of one of the first and second pulses, as measured from the signal corresponding to the wavelength indicated; and
$\Delta tp$ = the period of the pulse, as measured from the signal corresponding to the wavelength indicated.

In accordance with a further aspect of the invention, the method also includes the step of comparing the value of $R_{OS}$ produced with independently derived oxygen saturation curves to determine the oxygen saturation of the arterial blood in the tissue. Likewise, the step of producing an output indicative of the oxygen saturation determined can be included.

In accordance with another aspect of the invention, an apparatus for performing the method as outlined above is provided. In its most basic form, the apparatus includes a sampler for determining the signal magnitude at the plurality of sample times spaced over an interval greater than the period of one pulse. A processor then produces a single indication of the oxygen saturation from the sample times and signal magnitudes at those sample times. The apparatus may further include the detector, which produces the signals containing the oxygen saturation information, and a light source, which produces the light at two wavelengths. A red filter may be used to filter the light received by the detector and the signals may be amplified by a differential current-to-voltage amplifier before being sampled.

BRIEF DESCRIPTION OF THE DRAWINGS

The invention can best be understood by reference to the following portion of the specification, taken in conjunction with the accompanying drawings in which:

FIG. 4 is a graphical comparison of the incident light intensity to the emergent light intensity as modeled in FIG. 2;

FIG. 5 is a graphical comparison of the specific absorption coefficients for oxygenated hemoglobin and deoxygenated hemoglobin as a function of the wavelength of light transmitted therethrough;

FIG. 7 is a graphical comparison of empirically derived oxygen saturation measurements related to a measurable value determined by the oximeter;

FIG. 10 is a graphical plot as a function of time of the transmittance of light at the red wavelength through the finger;

FIG. 11 is a graphical plot as a function of time of the transmission of infrared light through the finger;

DETAILED DESCRIPTION

Figure 1:
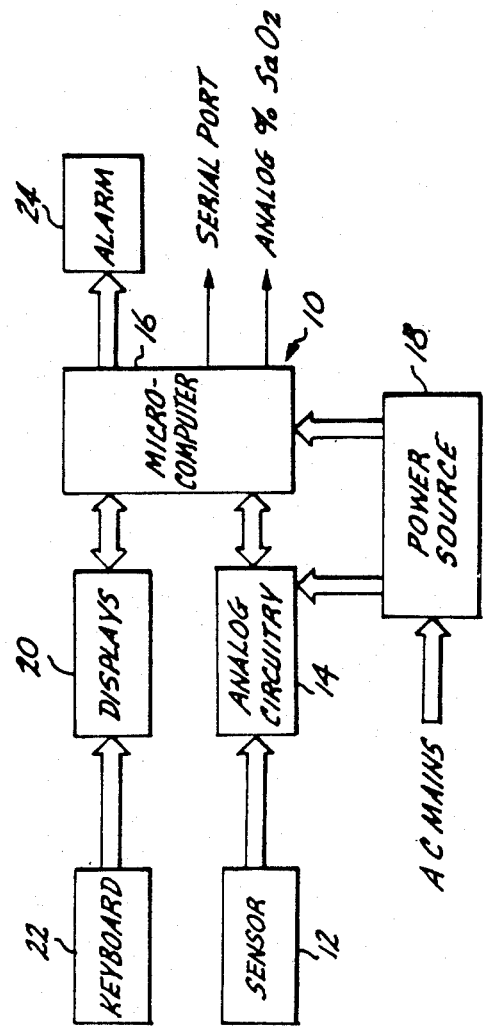
FIG. 1 is a block diagram of an oximeter including a sensor, input/output (I/O) circuit, microcomputer, alarm, displays, power supply, and keyboard.

Referring to the overall system block diagram shown in FIG. 1, a pulse transmittance oximeter 10 employing this invention includes a sensor 12, input/output (I/O) circuit 14, microcomputer 16, power source 18, displays 20, keyboard 22 and alarm 24. Before discussing these elements in detail, however, an outline of the theoretical basis of pulse transmittance oximetry as practiced by the oximeter of FIG. 1 is provided.

An understanding of the relevant theory begins with a discussion of the Beer-Lambert law. This law governs the absorption of optical radiation by homogeneous absorbing media and can best be understood with reference to FIGS. 2 and 3 in the following manner.

Figure 2:
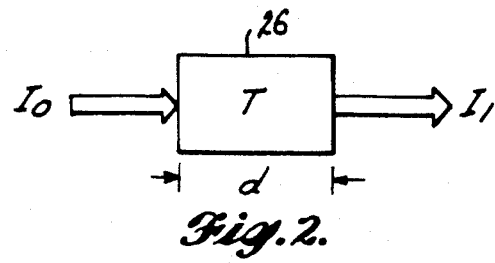
FIG. 2 is a block diagram illustrating the transmission of light through an absorptive medium.
Figure 3:
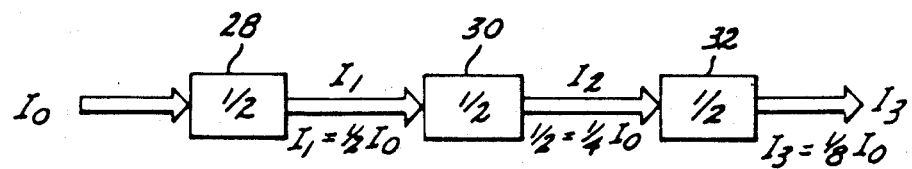
FIG. 3 is a block diagram illustrating the transmission of light throught the absorptive medium of FIG. 2, wherein the medium is broken up into elemental components.

As shown in FIG. 2, incident light having an intensity $I_0$ impinges upon an absorptive medium 26. Medium 26 has a characteristic absorbance factor A that indicates the attenuating affect medium 26 has on the incident light. Similarly, a transmission factor T for the medium is defined as the reciprocal of the absorbance factor, $1/A$. The intensity of the light $I_1$ emerging from medium 26 is less than $I_0$ and can be expressed functionally as the product $TI_0$. With medium 26 divided into a number of identical components, each of unit thickness (in the direction of light transmission) and hence the same transmission factor T, the effect of medium 26 on the incident light $I_0$ is as shown in FIG. 3.

There, medium 26 is illustrated as consisting of three components 28, 30, and 32. As will be appreciated, the intensity $I_1$ of the light emerging from component 28 is equal to the incident light intensity $I_0$ multiplied by the transmission factor T. Component 30 has a similar effect on light passing therethrough. Thus, because the light incident upon component 30 is equal to the product $TI_0$, the emergent light intensity $I_2$ is equal to the product $TI_1$ or $T \cdot I_0$. Component 32 has the same effect on light and, as shown in FIG. 3, the intensity of the emergent light $I_3$ for the entire medium 26 so modeled is equal to $TI_2$ or $T^3I_0$. If the thickness of medium 26 is n unit lengths, it can be modeled as including n components of unit thickness. It will then be appreciated that the intensity of light emerging from medium 26 can be designated $I_n$ and is equal to $T^n I_0$. Expressed as a function of the absorbance constant A, $I_n$ can also be written as $(1/A^n)I_0$.

From the preceding discussion, it will be readily appreciated that the absorptive effect of medium 26 on the intensity of the incident light $I_0$ is one of exponential decay. Because A may be an inconvenient base work with, $I_n$ can be rewritten as a function of a more convenient base, b, by recognizing that $A^n$ is equal to $B^{an}$, where is the absorbance coefficient of medium 26 per unit length. The term $\alpha$ is frequently referred to as the relative extinction coefficient and is equal to $\log_b A$.

Given the preceding discussion, it will be appreciated that the intensity of the light $I_n$ emerging from medium 26 can be expressed in base 10 as $I_0 10^{-\alpha_1 n}$, or in base e as $I_0 e^{-\alpha_2 n}$, where $\alpha_1$ and $\alpha_2$ are the appropriate relative extinction coefficients for base 10 and base e respectively. The effect that the thickness of medium 26 has on the emergent light intensity $I_n$ is graphically depicted in FIG. 4. If the light incident upon medium 26 is established as having unit intensity, FIG. 4 also represents the transmission factor T of the entire medium as a function of thickness.

The discussion above can be applied generally to the medium 26 shown in FIG. 2 to produce:

$$I_1 = I_0 e^{-\alpha l} \qquad (1)$$

where $I_1$ is the emergent light intensity, $I_0$ is the incident light intensity, $\alpha$ is the absorbance coefficient of the medium per unit length, l is the thickness of the medium in unit lengths, and the exponential nature of the relationship has arbitrarily been expressed in terms of base e. Equation (1) is commonly referred to as the Beer-Lambert law of exponential light decay through a homogeneous absorbing medium.

With this basic understanding of the Beer-Lambert law, a discussion of its application to the problems of pulse rate and hemoglobin oxygen saturation measurement is now presented. As shown in FIG. 5, the absorption coefficients for oxygenated and deoxygenated hemoglobin are different at every wavelength, except an isobestic wavelength. Thus, it will be appreciated that if a person's finger is exposed to incident light and the emergent light intensity measured, the difference in intensity between the two, which is the amount of light absorbed, contains information relating to the oxygenated hemoglobin content of the blood in the finger. The manner in which this information is extracted from the Beer-Lambert law is discussed below. In addition, it will be appreciated that the volume of blood contained within an individual's finger varies with the individual's pulse. Thus, the thickness of the finger also varies slightly with each arterial pulse, creating a changing path length for light transmitted through the finger. Because a longer lightpath allows additional light to be absorbed, time-dependent information relating to the difference between the incident and emergent light intensities can be used to determine the individual's pulse. The manner in which this information is extracted from the Beer-Lambert law is also discussed below.

As noted in the preceding paragraph, information about the incident and emergent intensities of light transmitted through a finger can be used to determine oxygen saturation and pulse rate. The theoretical basis for extracting the required information, however, is complicated by several problems. For example, the precise intensity of the incident light applied to the finger is not easily determined. Thus, it may be necessary to extract the required information independently of the intensity of the incident light. Further, because the changing volume of blood in the finger and, hence, thickness of the lightpath therethrough, are not exclusively dependent upon the individual's pulse, it is desirable to eliminate the changing path length as a variable from the computations.

Figure 6:
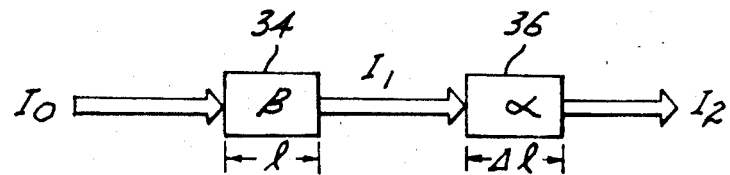
FIG. 6 is a block diagram illustrating the transmission of light through a block model of the components of a finger.

The manner in which the Beer-Lambert law is refined to eliminate the incident intensity and path length as variables is as follows. With reference to FIG. 6, a human finger is modeled by two components 34 and 36, in a manner similar to that shown in FIG. 3. Component 34 models the unchanging absorptive elements of the finger. This component includes, for example, bone, tissue, skin, hair, and baseline venous and arterial blood, and has a thickness designated d and an absorption $\beta$.

Component 36 represents the changing absorptive portion of the finger, the arterial blood volume. As shown, the thickness of this component is designated $\Delta l$, representing the variable nature of the thickness, and the arterial absorption of this component is designated $\alpha$ representing the arterial blood absorbance.

As will be appreciated from the earlier analysis with respect to FIG. 3, the light $I_1$ emerging from component 34 can be written as a function of the incident light intensity $I_0$ as follows:

$$I_1 = I_0 e^{-\beta l} \qquad (2)$$

Likewise, the intensity of light $I_2$ emerging from component 36 is a function of its incident light intensity $I_1$, and:

$$I_2 = I_1 e^{-\alpha \Delta l} \qquad (3)$$

Substitution of the expression for $I_1$ developed in euation (2) for that used in equation (3), when simplified, results in the following expression for the intensity $I_2$ of light emerging from the finger as a function of the intensity of light $I_0$ incident upon the finger;

$$I_2 = I_0 e^{-[\beta l + \alpha \Delta l]} \qquad (4)$$

Because our interest lies in the effect on the light produced by the arterial blood volume, the relationship between $I_2$ and $I_1$ is of particular interest. Defining the change in transmission produced by the arterial component 36 as $T_{\Delta A}$, we have:

$$T_{\Delta A} = (I_2/I_1) \quad (5)$$

Substituting the expressions for $I_1$ and $I_2$ obtained in equations (2) and (3), respectively, equation (5) becomes:

$$T_{\Delta A} = \frac{I_0 e^{-[\beta 1 + \alpha \Delta 1]}}{I_0 e^{-\beta 1}} \quad (6)$$

It will be appreciated that the $I_0$ term can be cancelled from both the numerator and denominator of equation (6), thereby eliminating the input light intensity as a variable in the equation. With equation (6) fully simplified, the change in arterial transmission can be expressed as:

$$T_{\Delta A} = e^{-\alpha \Delta l} \quad (7)$$

A device employing this principle of operation is effectively self-calibrating, being independent of the incident light intensity $I_0$.

At this point, a consideration of equation (7) reveals that the changing thickness of the finger, $\Delta l$, produced by the changing arterial blood volume still remains as a variable. The $\Delta l$ variable is eliminated in the following manner. For convenience of expression, the logarithms of the terms in equation (7) are produced with respect to the same base originally employed in equation (1). Thus, equation (7) becomes:

$$\ln T_{\Delta A} = \ln(e^{-\alpha \Delta l}) = -\alpha \Delta l \quad (8)$$

A preferred technique for eliminating the $\Delta l$ variable utilizes information drawn from the change in arterial transmission experienced at two wavelengths.

The particular wavelengths selected are determined in part by consideration of a more complete expression of the arterial absorbance $\alpha$: $\alpha = (\alpha_O)(OS) - (\alpha_D)(1-OS)$ $\quad (9)$ where $\alpha_O$ is the oxygenated arterial absorbance, $\alpha_D$ is the deoxygenated arterial absorbance, and OS is the hemoglobin oxygen saturation of the arterial blood volume. As will be appreciated from FIG. 5, $\alpha_O$ and $\alpha_D$ are substantially unequal at all light wavelengths in the red and near infrared wavelength regions except for an isobestic wavelength occurring at a wavelength of approximately 805 nanometers. With an arterial oxygen saturation OS of approximately 90 percent, it will be appreciated from equation (9) that the arterial absorbance $\alpha$ is 90 percent attributable to the oxygenated arterial absorbance $\alpha_O$ and 10 percent attributable to the deoxygenated arterial absorbance $\alpha_D$. At the isobestic point wavelength, the relative contribution of these two coefficients to the arterial absorbance $\alpha$ is of minimal significance in that both $\alpha_O$ and $\alpha_D$ are equal. Thus, a wavelength roughly approximating the isobestic wavelength of the curves illustrated in FIG. 5 is a convenient one for use in eliminating the change in finger thickness $\Delta l$ attributable to arterial blood flow.

A second wavelength is selected at a distance from the approximately isobestic wavelength that is sufficient to allow the two signals to be easily distinguished. In addition, the relative difference of the oxygenated and deoxygenated arterial absorbances at this wavelength is more pronounced. In light of the foregoing considerations, it is generally preferred that the two wavelengths selected fall within the red and infrared regions of the electromagnetic spectrum.

The foregoing information, when combined with equation (8) is used to produce the following ratio:

$$\frac{\ln T_{\Delta AR}}{\ln T_{\Delta AIR}} = \frac{-\alpha \Delta 1 @ \lambda_R}{-\alpha \Delta 1 @ \lambda_{IR}} \quad (10)$$

where $T_{\Delta AR}$ equals the change in arterial transmission of light at the red wavelength $\lambda_R$ and $T_{\Delta AIR}$ is the change in arterial transmission at the infrared wavelength $\lambda_{IR}$. It will be appreciated that if two sources are positioned at substantially the same location on the finger, the length of the lightpath through the finger is substantially the same for the light emitted by each. Thus, the change in the lightpath resulting from arterial blood flow, $\Delta l$, is substantially the same for both the red and infrared wavelength sources. For that reason, the $\Delta l$ term in the numerator and denominator of the right-hand side of equation (10) cancel, producing:

$$\frac{\ln T_{\Delta AR}}{\ln T_{AIR}} = \frac{\alpha @ \lambda_R}{\alpha @ \lambda_{IR}} \quad (11)$$

As will be appreciated, equation (11) is independent of both the incident light intensity $I_0$ and the change in finger thickness $\Delta l$ attributable to arterial blood flow. The foregoing derivations form the theoretical basis of pulse oximetry measurement. Because of the complexity of the physiological process, however, the ratio indicated in equation (11) does not directly provide an accurate measurement of oxygen saturation. The correlation between the ratio of equation (11) and actual arterial blood gas measurements is, therefore, relied on to produce indication of the oxygen saturation. Thus, if the ratio of the arterial absorbance at the red and infrared wavelengths can be determined, the oxygen saturation of the arterial blood flow can be extracted from such independently derived calibration curves in a manner independent of $I_0$ and $\Delta l$.

For simplicity, a measured ratio $R_{OS}$ is defined from equation (11) as:

$$\text{Ratio} = R_{OS} = \frac{\alpha @ \lambda_R}{\alpha @ \lambda_{IR}} \quad (12)$$

It is this value for $R_{OS}$ that is plotted on the x-axis of independently derived oxygen saturation curves, as shown in FIG. 7 and discussed in greater detail below, with the hemoglobin oxygen saturation being referenced on the y-axis.

The preceding discussion treats the absorption coefficients $\beta$ and $\alpha$ for the unchanging and changing absorptive components in the finger as being constant as a function of time. It has been found, however, that the production of highly accurate oxygen saturation information requires that the time dependency of $\beta$ and $\alpha$ be considered. Thus, the discussion below of the manner in which $R_{OS}$ is measured begins with a brief outline of the time-dependent functions $\beta(t)$ and $\alpha(t)$. The effect of these functions is then included in the synthesis of an easily measurable expression for $R_{OS}$.

Variations in the absorption coefficients as a function of time may result for a variety of reasons. For example, changes in patient physiology other than arterial blood flow characteristics may significantly affect the "fixed" component absorption coefficient $\beta(t)$. Similarly, relatively small changes in blood composition may significantly affect the arterial absorption coefficient $\alpha(t)$.

Figure 8:
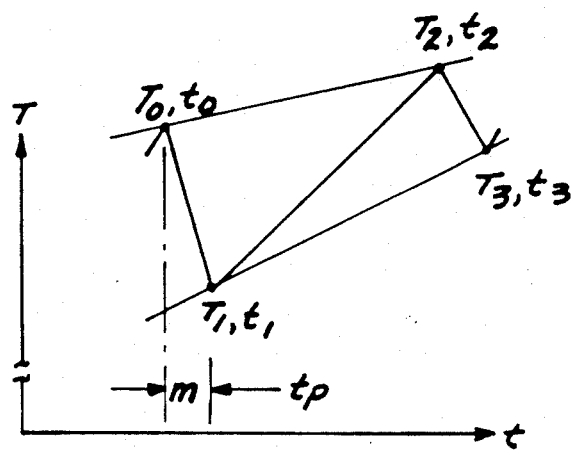
FIG. 8 is a graphical illustration of the transmittance of light, through tissue supplied with arterial blood, as a function of time over an interval encompassing two diastoles and systoles.

The transmission of light through a finger is illustrated in FIG. 8, as a function of time, and shows the effect of the fixed and arterial absorption coefficients $\beta(t)$ and $\alpha(t)$, expressed as a function of time. The transmittance plotted in FIG. 8 includes two maxima and minima corresponding to adjacent diastoles and systoles of the arterial blood flow in the finger. A first diastole occurs at time $t_0$ and the transmittance at that point is designated $T_0$. As will be appreciated, arterial blood volume is at a minimum during diastole and, therefore, the transmittance $T_0$ is at a maximum. That diastole is followed by a systole at time $t_1$ where the transmittance is indicated as $T_1$. Because arterial blood volume is at a maximum at systole, the amount of light absorbed is likewise at a maximum and the transmittance $T_1$ is at a minimum. After $t_1$, a second diastole occurs at time $t_2$ having a transmittance of $T_2$ and is followed by a systole at time $t_3$ having a transmittance of $T_3$.

Turning now to the derivation of a measurable expression of $R_{OS}$, as will be appreciated from the previous discussion of the Beer-Lambert law, the intensity of light emerging from the finger $I_2$ can be expressed as a function of the incident light intensity $I_0$ in the following manner:

$$I_2 = I_0 e^{-[\beta(t) + \alpha(t)]} \tag{13}$$

Adopting the convention of FIG. 8, wherein subscripts are used to identify points in time, the relationship of equation (13) is expressed at a particular time n as:

$$I_{2n} = I_0 e^{-[\beta(t_n) + \alpha(t_n)]} \tag{14}$$

The lack of a subscript n for the incident light intensity $I_0$ indicates that $I_0$ is presumed constant and not a function of time.

To obtain a measurable expression of $R_{OS}$, more complete expressions of the two absorption coefficients as a function of time are needed. This requires that several assumptions be made. As apparent from FIG. 8, any change in transmittance between adjacent diastoles is determined substantially entirely by the changing attenuation in emergent light intensity $I_2$ produced by the fixed absorptive component. Thus, the change in transmittance between adjacent diastoles is proportional to the change in the absorption coefficient $\beta(t)$ and, for the relatively short interval between adjacent diastoles, can be approximated as a straight line. Expanding the expression of $\beta$ as a function of time, we get:

$$\beta(t) = \beta_0 g(t) \tag{15}$$

where $\beta_0$ is the magnitude of the absorption coefficient at time $t_0$ and $g(t)$ is an expression of the change in $\beta$ as a function of time following time $t_0$. As noted, this change can be approximated linearly and, therefore, can be expressed as:

$$g(t) = 1 + b(t - t_0) \tag{16}$$

where b is the slope of the linear change in transmittance between the diastoles at $t_0$ and $t_2$. Arbitrarily establishing time $t_0$ as a reference point having a zero value, substitution of equation (16) into equation (15) produces:

$$\beta(t) = \beta_0(1 + bt) \tag{17}$$

An expanded expression of the arterial absorption coefficient $\alpha$ as a function of time can be produced in a similar manner. As will be appreciated from FIG. 8, the change in transmittance between the systoles at times $t_1$ and $t_3$ is proportional both to the changing fixed and arterial absorptive components in the finger. With $\beta(t)$ expressed as a linear function during this interval, the change in transmittance due to the arterial absorption coefficient $\alpha(t)$ can likewise be approximated as a linear function. Therefore, $\alpha(t)$ can be expressed more completely as:

$$\alpha(t) = \alpha_0 K \Delta l f(t) \tag{18}$$

where $\alpha_0$ is the magnitude of the arterial absorption coefficient at time $t_0$, K is a constant, $\Delta l$ is the length of the path through which the light must pass as a function of blood volume, and $f(t)$ is an expression of the change in $\alpha$ as a function of time following $t_0$. Assuming that $f(t)$ is approximately linear over a short interval following $t_0$, it can be expressed more completely as: $f(t) = 1 + a(t - t_0)$ where a is the portion of the slope of the transmittance between times $t_1$ and $t_3$ that is attributable to the change in $\alpha(t)$ rather than $\beta(t)$. Recognizing that time $t_0$ has been established as a reference point having a zero value, substitution of equation (19) into equation (18) yields:

$$\alpha(t) = \alpha_0 K \Delta l (1 + at) \tag{20}$$

As defined in equation (12), the ratio $R_{OS}$, from which the oxygen saturation is determined by reference to empirically derived calibration curves, is a function of the arterial absorption coefficient at the R and IR wavelengths. From equation (20), it will be appreciated that further development is required to produce an expression of $R_{OS}$ in terms of parameters that can be easily measured by instrumentation. More particularly, an expression of $R_{OS}$ that is independent of $\alpha_0$, $\beta_0$, K, $\Delta l$, a, and b is needed. Because the transmittances at adjacent systoles and diastoles can be represented as voltages, an expression of $R_{OS}$ dependent only upon the transmittances is sought. In that regard, the following equations are developed to express the variables to be eliminated (e.g., $\alpha_0$) as a function of the transmittances.

As a first step in that process, the transmittances at the adjacent diastoles and systoles illustrated in FIG. 8 are developed using the Beer-Lambert law. As will be appreciated, the transmittance $T_n$ at any time $t_n$ can be expressed as:

$$T_n = (I_{2n}/I_0) \tag{21}$$

Substitution of equation (14) into equation (21) produces:

$$T_n = \frac{I_0 e^{-[\beta(t_n) + \alpha(t_n)]}}{I_0} = e^{-[\beta(t_n) + \alpha(t_n)]} \tag{22}$$

As noted previously, at the diastoles, a minimum blood volume is present. This minimum blood volume causes the $\Delta l$ term in the expression of the arterial absorption coefficient shown in equation (20) to approach a zero value. Therefore, at times $t_0$ and $t_2$, the expression of the arterial absorption coefficient as a function of time in the exponential term of equation (22) goes to zero and can be ignored. Thus, the transmittance at time $t_0$ can be expressed as:

$$T_0 = e^{-[\beta(t0)+0]} = e^{-\beta(t0)} \tag{23}$$

Substitution of equation (17) into equation (23) produces:

$$T_0 = e^{-\beta 0(1+bt0)} = e^{-\beta 0(1+b(0))} = e^{-\beta 0} \tag{24}$$

given the establishment of the time $t_0$ as a reference point having a zero value.

At systole, both absorption coefficients remain in the exponential term of equation (22). Therefore, the substitution of equations (17) and (20) into equation (22) allows the transmittance at time $t_1$ to be expressed as:

$$T_1 = e^{-[\beta(t1)+\alpha(t1)]} = e^{-[\beta 0(1+bt1)+\alpha 0 K \Delta l(1+at1)]} \tag{25}$$

Returning to the second diastole, because the value of $\Delta$ approaches zero, the arterial absorption coefficient in equation (22) is again substantially equal to zero and the substitution of equation (17) into equation (22) produces a transmittance at time $t_2$ that is equal to:

$$T_2 = e^{[\beta(t2)+\alpha(t2)]} = e^{-[\beta 0(1+bt2)+0]} = e^{-\beta 0(1+bt2)} \tag{26}$$

Substitution of equations (17) and (20) into equation (22) allows the transmittance at the second systole, occurring at time $t_3$, to be expressed as:

$$T_3 = e^{-[\beta(t3)+\alpha(t3)]} = e^{-[\beta 0(1+bt3)+\alpha 0 K \Delta l(1+at3)]} \tag{27}$$

Thus, we now have expressions for the transmittances at adjacent systoles and diastoles expressed as functions of the variables that are to be eliminated.

To simplify the expressions of equations (24), (25), (26), and (27), several expressions relating to the timing of the systoles and diastoles are developed. For example, the pulse interval between adjacent systoles or diastoles can be designated $t_p$ and, as will be appreciated from FIG. 8, expressed as:

$$t_p = t_2 - t_0 = t_2 - 0 = t_2 = 1 \tag{28}$$

where time $t_0$ has been established as a reference point having a zero value, and a unit pulse duration has been assumed. Thus, as a result of these arbitrary assignments, we have:

$$t_0 = 0 \text{ and } t_2 = 1 \tag{29}$$

From FIG. 8, it will be appreciated that the ratio of the time between an adjacent diastole and systole to the time between adjacent diastoles, designated m, can be expressed as:

$$m = \frac{t_{systole\ 1} - t_{diastole\ 0}}{t_{diastole\ 2} - t_{diastole\ 0}} = \frac{\Delta ts}{\Delta tp} = \frac{t_1 - t_0}{t_2 - t_0} \tag{30}$$

Equation (30) can be simplified by use of the relationships expressed at (29), resulting in:

$$m = \frac{t_1 - 0}{1 - 0} = t_1 \tag{31}$$

Because the interval between an adjacent systole and diastole will not change significantly between adjacent pulses, the ratio m can also be expressed as:

$$m = \frac{t_{systole\ 3} - t_{diastole\ 2}}{t_{diastole\ 2} - t_{diastole\ 0}} = \frac{\Delta ts}{\Delta tp} = \frac{t_3 - t_2}{t_2 - t_0} \tag{32}$$

Substitution of the relationships expressed at equation (29) into equation (32), when simplified, yields:

$$m = \frac{t_3 - 1}{1 - 0} = t_3 - 1 \tag{33}$$

and:

$$t_3 = m + 1 \tag{34}$$

In summary, the timing of the adjacent systoles and diastoles can be expressed in simplified form as:

$$t_0 = 0,\ t_1 = m,\ t_2 = 1,\ t_3 = m + 1 \tag{35}$$

Substitution of the values expressed in (35) for the transmittances determined in equations (24), (25), (26) and (27) produce the following expressions for transmittance:

$$T_0 = e^{-\beta 0} \tag{36}$$

$$T_1 = e^{-[\beta 0(1+bm)+\alpha 0 k \Delta l(1+am)]} \tag{37}$$

$$T_2 = e^{-[\beta 0(1+b)]} \tag{38}$$

$$T_3 = e^{-[\beta 0(1+b(1+m))+\alpha 0 k \Delta l(1+a(1+m))]} \tag{39}$$

While the development of the transmittance equations (36)–(39) brings us closer to a measurable expression of $R_{OS}$, further simplification is still required. For that reason, the ratio between the transmittances at an adjacent systole and diastole, as well as the ratio between the transmittance at adjacent systoles and at adjacent diastoles, will now be computed. This process eliminates terms from the exponentials, making them more manageable, and its use in producing an easily measurable expression of $R_{OS}$ will be shown below.

The ratio of transmittances between an adjacent systole and diastole can be expressed and simplified in the following manner:

$$\frac{T_1}{T_0} = \frac{e^{-[\beta 0(1+bm)+\alpha 0 k \Delta l(1+am)]}}{e^{-\beta 0}} = e^{-[\beta 0 bm + \alpha 0 k \Delta l(1+am)]} \tag{40}$$

where the values for $T_1$ and $T_0$ were obtained from equations (37) and (36), respectively.

Similarly, the ratio between adjacent diastolic transmittances is produced from the equations (38) and (36) as:

$$\frac{T_2}{T_0} = \frac{e^{-\beta 0(1+b)}}{e^{-\beta 0}} = e^{-\beta 0 b} \tag{41}$$

Finally, the ratio between adjacent systolic transmittances is produced from equations (39) and (37) as:

$$\frac{T_3}{T_1} = \frac{e^{-[\beta_0(1+b(1+m))+\alpha_0 k\, l(1+a(1+m))]}}{e^{-[\beta_0(1+bm)+\alpha_0 k\, l(1+am)]}} = e^{-(\beta_0 b + \alpha_0 k \Delta la)} \quad (42)$$

Because exponentials are somewhat awkward to work with, equations (40), (41) and (42) can be simplified by taking the natural logarithm of each side of the equations. Thus, we have:

$$\ln\frac{T_1}{T_0} = -[\beta_0 bm + \alpha_0 k\Delta l(1 + am)] \quad (43)$$

$$\ln\frac{T_2}{T_0} = -\beta_0 b \quad (44)$$

$$\ln\frac{T_3}{T_1} = -(\beta_0 b + \alpha_0 k \Delta la) \quad (45)$$

As noted earlier, to develop an easily measurable expression for $R_{OS}$ requires that expressions for $\alpha_0$, k, and $\Delta l$ be produced as a function of the transmittances. To this end, equations (43) and (45) can be rewritten to produce:

$$\alpha_0 k \Delta l = \frac{-[\ln(T_3/T_1) + b\,\beta_0]}{a} = \frac{-[\ln(T_1/T_0) + bm\,\beta_0]}{1 + am} \quad (46)$$

Equation (46), however, still includes a number of terms which cannot be directly measured. Thus, an equation independent of the terms a, b, and $\beta_0$ is desired. If the negative signs are canceled and each of the two right-hand portions of equation (46) multiplied by the term $a(1+am)$, equation (46) can be developed into the following relationship:

$$(1+am)[ln(T_3/T_1)+b\beta_0]=a[ln(T_1/T_0)+bm\beta_0] \quad (47)$$

Equation (47) is simplified in equations (48)–(51) as follows:

$$ln(T_3/T_1)+b\beta_0+amln(T_3/T_1)+amb\beta_0 \\ =a[ln(T_1/T_0)+bm\beta_0] \quad (48)$$

$$ln(T_3/T_1)+b\beta_0+a[mln(T_3/T_1)+mb\beta_0 \\ ]=a[ln(T_1/T_0)+bm\beta_0] \quad (49)$$

$$ln(T_3/T_1)+b\beta_0=a[ln(T_1/T_0)+bm\beta_0-mln(T_3/T_1) \\ -mb\beta_0] \quad (50)$$

$$ln(T_3/T_1)+b\beta_0=a[ln(T_1/T_0)-mln(T_3/T_1)] \quad (51)$$

Equation (51) can then be solved for "a" in the following manner:

$$a = \frac{\ln(T_3/T_1) + b\,\beta_0}{\ln(T_1/T_0) - m\ln(T_3/T_1)} \quad (52)$$

Substitution of equation (44) into equation (52) produces:

$$a = \frac{\ln(T_3/T_1) - \ln(T_2/T_0)}{\ln(T_1/T_0) - m\ln(T_3/T_1)} \quad (53)$$

As will be remembered, equation (46) provides:

$$\alpha_0 k \Delta l = \frac{-\ln(T_1/T_0) - bm\,\beta_0}{1 + am} \quad (54)$$

and the substitution of equations (44) and (53) into equation (54) produces:

$$\alpha_0 k \Delta l = \frac{+\ln(T_1/T_0) + m\ln(T_2/T_0)}{1 + m\left[\dfrac{\ln(T_3/T_1) - \ln(T_2/T_0)}{\ln(T_1/T_0) - m\ln(T_3/T_1)}\right]} \quad (55)$$

As will be appreciated from equations (10), (11) and (12) of the basic theoretical discussions, the ratio used in oxygen saturation measurement, $R_{OS}$, can be expressed as:

$$R_{OS} = \frac{\alpha\Delta l\ @\ \lambda R}{\alpha\Delta l\ @\ \lambda IR} = \frac{\alpha\Delta^1\ @\ \lambda_1}{\alpha\Delta l\ @\ \lambda_2} \quad (56)$$

Expanding the arterial absorption coefficient $\alpha$ in terms of the foregoing nomenclature, equation (56) becomes:

$$R_{OS} = \frac{\alpha_0^k \Delta^1\ @\ \lambda_1}{\alpha_0 k \Delta l\ @\ \lambda_2} \quad (57)$$

As will be appreciated, substitution of equation (55) into the numerator and denominator of equation (57) results in:

$$R_{OS} = \frac{\dfrac{\ln(T_1/T_0) - m\ln(T_2/T_0)}{1 + m[(\ln(T_3/T_1) - \ln(T_2/T_0))/(\ln(T_1 T_0) - m\ln(T_3/T_1))]}\ @\ \lambda_1}{\dfrac{\ln(T_1/T_0) - m\ln(T_2/T_0)}{1 + m[\ln(T_3/T_1) - \ln(T_2/T_0)/(\ln(T_1/T_0) - m\ln(T_3/T_1))]}\ @\ \lambda_2} \quad (58)$$

Thus, an expression for the oxygen saturation ratio is produced that is independent of $\alpha$, $\beta$, k, and $\Delta l$. As will be readily appreciated, however, the resultant expression is somewhat unwieldy. Therefore, a more concise expression is desired. In that regard, simplification of the numerator and denominator, identical except for the required solution at different wavelengths, is desired. This common term is simply the right-hand side of equation (55) and, for convenience, is designated $R_\lambda$. $R_\lambda$ may be simplified as follows:

$$R_\lambda = \frac{[\ln(T_1T_0) - m\ln(T_3T_1)]}{[\ln(T_1/T_0) - m\ln(T_3/T_1)]} \times \frac{[\ln(T_1/T_0) - m\ln(T_2/T_0)]}{1 + m\left[\frac{\ln(T_3/T_1) - \ln(T_2/T_0)}{\ln(T_1T_0) - m\ln(T_3T_0)}\right]} \quad (59)$$

$$= \frac{[\ln(T_1/T_0) - m\ln(T_3/T_1)][\ln(T_1/T_0) - m\ln(T_2/T_0)]}{\ln(T_1/T_0) - m\ln(T_3/T_1) + m\ln(T_3/T_1) - m\ln(T_2T_0)}$$

$$= \frac{[\ln(T_1T_0) - m\ln(T_3/T_1)][\ln(T_1T_0) - m\ln(T_2/T_0)]}{[\ln(T_1/T_0) - m\ln(T_2/T_0)]}$$

$$= \ln(T_1T_0) - m\ln(T_3/T_1)$$

where $\ln(T_1/T_0)$ can be considered an uncorrected value of $R_\lambda$ and $-m\ln(T_3/T_1)$ is a corrective term. Given this expression of $R_\lambda$, $R_{OS}$ can be written:

$$R_{OS} = \frac{\ln(T_1/T_0) - m\ln(T_3/T_1) \ @ \ \lambda_1}{\ln(T_1/T_0) - m\ln(T_3/T_1) \ @ \ \lambda_2} \quad (60)$$

Another expression of $R_{OS}$ can be produced from (59) by recognizing that $\ln(y/x) = -\ln(x/y)$. Thus, $R_\lambda$ can be written:

$$R_\lambda = -[ln(T_0/T_1) + mln(T_3/T_1)] \quad (61)$$

Further, because $(z)\ln(x/y) = \ln(x/y)^z$, equation (61) can be reduced to:

$$R_\lambda = -[ln(T_0/T_1) + ln(T_3/T_1)^m] \quad (62)$$

which can be approximated as:

$$R_\lambda \approx -[\ln(T_0/T_1) + \ln(1 + m(T_3/T_1 - 1))] \quad (63)$$

Given that $\ln x + \ln y = \ln xy$, equation (63) can further be reduced to:

$$R_\lambda \approx -\ln[(T_0/T_1)(1 + m(T_3/T_1 - 1))] \quad (64)$$

Substitution of $R_\lambda$, as more simply expressed in equation (64), back into the numerator and denominator of equation (58) yields:

$$R_{OS} = \frac{\ln[(T_0/T_1)(1 + m(T_3/T_1 - 1))] \ @ \ \lambda_1}{\ln[(T_0/T_1)(1 + m(T_3/T_1 - 1))] \ @ \ \lambda_2} \quad (65)$$

Figure 9:
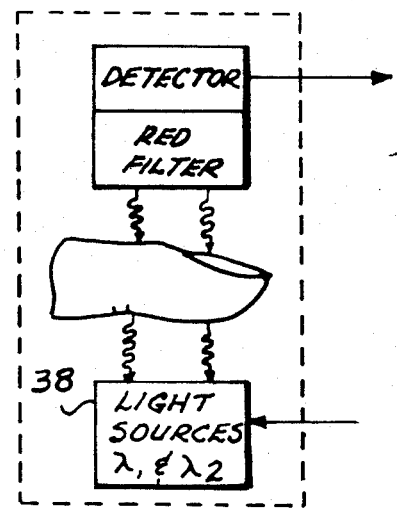
FIG. 9 is a schematic illustration of the transmission of light at two wavelengths through a finger in accordance with the invention.

As shown in FIG. 9, a detector 38 placed on the side of a finger opposite red and infrared wavelength light sources 40 and 42 receives light at both wavelengths transmitted through the finger. The intensity of the red wavelength light received is plotted in FIG. 10 as a function of time. With a unitized input intensity, FIG. 10 is essentially a more expansive depiction of the transmittance of FIG. 8, considered for a particular wavelength. The intensity varies with, among other things, the arterial pulse, and has high and low values $R_H$ and $R_L$. $R_L$ occurs substantially at systole, when arterial blood volume is at its greatest. $R_H$, on the other hand, occurs substantially at diastole, when the arterial blood volume is lowest. As will be appreciated from FIG. 11, the intensity of the infrared wavelength light received at detector 38 varies in a similar manner and has maxima and minima identified as $IR_H$ and $IR_L$, respectively. As will be discussed in greater detail below, detector 38 produces an output signal that includes information about $R_H$, $R_L$, $IR_H$, and $IR_L$, thereby allowing values for $T_0$, $T_1$, $T_2$, and $T_3$ to be determined. For convenience of expression, $T_0$ may be designated $V_H$ (indicating the voltage level at $R_H$ or $IR_H$), while $T_1$ may be designated $V_L$ (indicating the voltage level at $R_L$ or $IR_L$). Similarly, the change in systolic transmittance over one pulse, $T_3 - T_1$, may be designated $\Delta V$. Thus, in derivative form:

$$\frac{T_3}{T_1} - 1 = \frac{T_3 - T_1}{T_1} = \frac{\Delta V}{V_L} \quad (66)$$

In addition, m can be expressed as:

$$m = \frac{\Delta ts}{\Delta tp} \quad (67)$$

Substitution of equations (66) and (67) into equation (64) yields the equivalent of equation (65) in derivative form:

$$R_{OS} = \frac{\ln[(V_H/V_L)(1 + (\Delta ts/\Delta tp)(\Delta V/V_L))] \ @ \ \lambda_1}{\ln[(V_H/V_L)(1 + (\Delta ts/\Delta tp)(\Delta V/V_L))] \ @ \ \lambda_2} \quad (68)$$

where $\lambda_1$ and $\lambda_2$ are broader expressions of the wavelengths of light to which the finger is exposed. Equation (68) can then be simplified to:

$$R_{OS} = \frac{\ln[(V_H/V_L)((V_L + \Delta V \Delta ts/\Delta tp)/V_L)] \ @ \ \lambda_1}{\ln[(V_H/V_L)((V_L + \Delta V \Delta ts/\Delta tp)/V_L)] \ @ \ \lambda_2} \quad (69)$$

The expression for $R_{OS}$ shown in equation (69) is, however, only one expression useful in the performance of multiple-pulse measurement oximetry. More particularly, as will be appreciated from equation (59) in FIG. 8, the development of equation (69) introduces a one-pulse time lag between the occurrence of the first information used in the computation of $R_{OS}$ and the actual computation of $R_{OS}$. To avoid this one-pulse time lag, another expression of $R_{OS}$ is produced. Initially, we rely upon the fact that the time-dependent nature of the absorption coefficients is linear over the relatively small interval defined between pulses. Therefore, the corrective term $m\ln(T_3/T_1)$ of equation (59) can be included in the computation of $R_{OS}$ for the pulse defined by $T_2$ and $T_3$, as well as for the pulse defined by $T_0$ and $T_1$. This use of the corrective factor applicable to the preceding pulse for the current pulse detected allows equation (59) to be reexpressed as:

$$R_\lambda \approx \ln\frac{T_2}{T_3} + m\ln\frac{T_3}{T_1} \approx \ln\left[\frac{T_2}{T_3}(1 + m(T_3/T_1 - 1))\right] \quad (70)$$

From equations (66) and (67) it will be appreciated that the equivalent of equation (70) can be expressed with derivatives as:

$$R_\lambda \cong \ln\left[\frac{V_H}{V_L}(1 + (\Delta ts/\Delta tp)(\Delta V/V_L))\right] \quad (71)$$

Use of the relationship $1+x=1/(1-x)$ allows us to express equation (71) as:

$$R_\lambda \cong \ln\left[\frac{V_H}{V_L - \frac{\Delta ts \Delta V}{\Delta tp}}\right] \quad (72)$$

and, thus, $R_{OS}$ can be expressed as:

$$R_{OS} = \frac{\ln\left[\frac{V_H}{V_L - (\Delta ts \Delta V/\Delta tP)}\right] @ \lambda_1}{\ln\left[\frac{V_H}{V_L - (\Delta ts \Delta V/\Delta tp)}\right] @ \lambda_2} \quad (73)$$

which is our currently preferred manner of computing $R_{OS}$.

A second expression useful in multiple pulse oximetry retains the one-pulse delay but includes an empirically useful averaging of the high and low peaks. According to this technique, the second term of equation (59) is modified resulting in:

$$R_\lambda = \ln(T_0/T_1) + (m/2)[\ln(T_2/T_0) + \ln(T_3/T_1)] \quad (74)$$
$$\cong \ln[T_0/T_1 (1 + (m/2)(T_2/T_0 - 1) + (m/2)(T_3/T_1 - 1))]$$

Thus, $R_{OS}$ may be expressed as:

$$R_{OS} = \quad (75)$$

$$\frac{\ln[T_0/T_1 (1 + (m/2)(T_2/T_0 - 1) + (m/2)(T_3/T_1 - 1))] @ \lambda_1}{\ln[T_0/T_1 (1 + (m/2)(T_2/T_0 - 1) + (m/2)(T_3/T_1 - 1))] @ \lambda_2}$$

As will be appreciated, equation (70) can be expanded to include additional terms, increasing accuracy at the expense of computational complexity. Thus, equation (70) can be written:

$$R_\lambda = \ln\left[\frac{T_2}{T_3}\left(1 + \sum_{i,j,k} m_k\left(\frac{T_i}{T_j} - 1\right)\right)\right] \quad (76)$$

where i, j, and k are positive and negative integers. $R_{OS}$ can then be expressed as:

$$R_{OS} = \frac{\ln\left[T_2/T_3\left(1 + \sum_{i,j,k} m_k (T_i/T_j - 1)\right)\right] @ \lambda_1}{\ln\left[T_2/T_3\left(1 + \sum_{i,j,k} m_k (T_i/T_j - 1)\right)\right] @ \lambda_2} \quad (77)$$

An expression of $R_{OS}$ can also be developed that is free from the one-pulse lag discussed above and includes the empirically useful averaging of the high and low peaks. As will be appreciated from the discussion above, according to this technique, equation (70) can be developed into:

$$R_\lambda = \ln(T_2/T_3) + (m/2)[\ln(T_2/T_0) + \ln(T_3/T_1)] \quad (78)$$
$$\cong \ln\left[\frac{T_2}{T_3}(1 + (m/2)(T_2/T_0 - 1) + (m/2)(T_3/T_1 - 1))\right]$$

Figure 17:
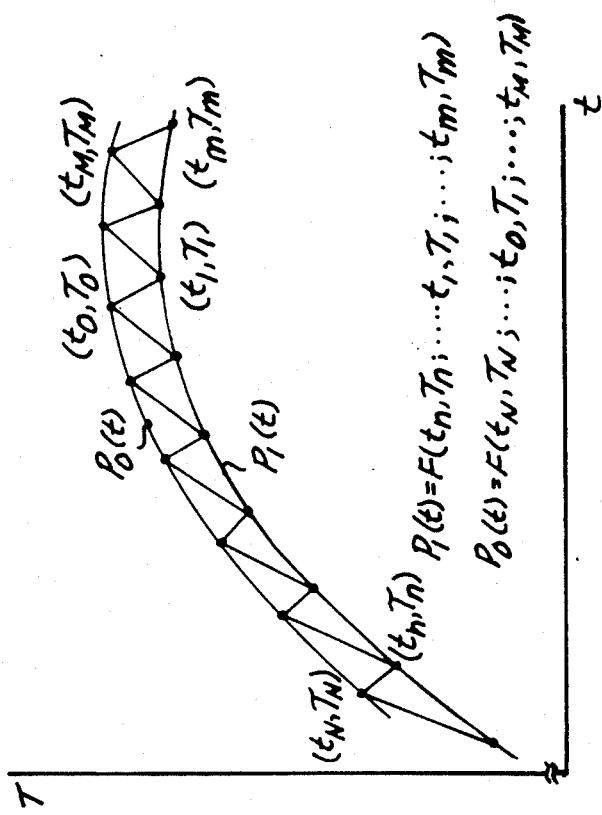
FIG. 17 depicts a signal produced in response to absorption coefficients that exhibit nonlinear changes, plotted as a function of time.

The formulations outlined above are based on the linear interpolation of two pulses and work well for relatively slow changes in the absorption coefficients with time. For additional accuracy when the absorption coefficients change more rapidly, a higher order interpolation technique can be used. More particularly, with respect to FIG. 17, a plurality of pulses of a signal produced in response to absorption coefficients that exhibit nonlinear change with time is illustrated. Thus, the variation in $\beta(t)$ over the interval may be represented as some interpolating function $P_0(t)$ and the combined change attributable to the time-dependency of $\beta(t)$ and $\alpha(t)$ represented as some interpolating function $P_1(t)$.

As will be appreciated from the preceding discussions and particularly equation (59), a representation of $R_\lambda$ incorporating these nonlinear variations can be produced that is expressed as:

$$R_{80} = \ln(T_0/T_1) + \ln[P_1(t_1)/P_1(t_0)] \quad (79)$$

where $P_1(t_1)$ is equal to $T_1$ and $P_1(t_0)$ is a term that must be interpolated from the nonlinear change in absorption coefficients. Thus, $R_{OS}$ may be written:

$$R_{OS} = \frac{(\ln(T_0/T_1) + \ln[P_1(t_1)/P_1(t_0)] @ \lambda_1}{\ln(T_0/T_1) + \ln[P_1(t_1)/P_1(t_0)] @ \lambda_2} \quad (80)$$

Equation (74) can be further expressed with averaged high and low peaks as:

$$R_\lambda = \ln(T_0/T_1) + \tfrac{1}{2}[\ln(P_1(t_1)/P_1(t_0)) + \ln(P_0(t_1)/P_0(t_0))] \quad (81)$$

where $P_1(t_1)$ is equal to $T_1$, $P_0(t_0)$ is equal to $T_0$, and both $P_1(t_0)$ and $P_0(t_1)$ must be interpolated from the nonlinear functions. This allows $R_{OS}$ to be computed as:

$$R_{OS} = \quad (82)$$

$$\frac{\ln(T_0/T_1) + \tfrac{1}{2}[\ln(P_1(t_1)/P_1(t_0)) + \ln(P_0(t_1)/P_0(t_0))] @ \lambda_1}{\ln(T_0/T_1) + \tfrac{1}{2}[\ln(P_1(t_1)/P_1(t_0)) + \ln(P_0(t_1)/P_0(t_0))] @ \lambda_2}$$

An advantage of the foregoing measurement techniques is that in every form produced, the corrected value of $R_\lambda$ includes an initial uncorrected term and a corrective term. When $\beta(t)$ and $\alpha(t)$ are substantially constant with respect to time, the corrective term equals zero and does not affect the otherwise normally calculated value of $R_\lambda$. With $\beta(t)$ and $\alpha(t)$ changing, however, the corrective term always improves the uncorrected value of $R_\lambda$. Further, even if the correction provided is incomplete, an effect like averaging is produced but within near-zero time lag. Therefore, a measurement that accurately tracks the changes in $\beta(t)$ and $\alpha(t)$ is produced without time lag, allowing real-time information to be developed.

It should be noted that the technique described does not necessarily require an accurately measured value for m. Even if the value of m is only approximated, a significant improvement over uncorrected computations results. For maximum correction, however, m can be measured. For example, m can be set initially, updated only occasionally, or continually updated.

Because $\Delta V$ is the difference in $V_L$ between adjacent systoles, determination of $R_{OS}$ in this manner, unlike prior art techniques, requires that information be extracted from multiple pulses rather than one. Thus, the microprocessor software must not only determine the magnitude of the voltage produced in response to the transmittance detected at an adjacent diastole and systole, but must also determine that corresponding to a second pulse systole. In addition, timing information indicating pulse duration as well as the interval between an adjacent diastole and systole must be obtained and all the information combined to determine $R_{OS}$. As will be appreciated, the determination of oxygen saturation in this manner also differs from prior art techniques, such as that disclosed by Wilber, by using both the DC and AC components of the signals.

The advantage of two-pulse measurement oximetry can be roughly described in the following manner. It has been found that measurements produced with single-pulse measurement oximetry from dynamic data may have an error of greater than 4.5 percent until 10 to 15 pulses have been processed. This error may even exceed 8 percent intially. It has been found that the preceding described two pulse measurement oximetric technique reduces the maximum error to slightly above 3 percent initially and to less than ½ percent are two pulses are measured.

The implementation of this two-pulse measurement technique will be readily understood by one of ordinary skill in conjuncton with the following brief discussion of the oximetric circuitry. The first component of oximeter 10 to be discussed is sensor 12.

The function of sensor 12 is substantially to provide the desired orientation of light sources 40 and 42, for example, light-emitting diodes (LEDs), and light detector 38 with respect to a suitable portion of a patient's body. For example, the sensor must align LEDs 40 and 42 with detector 38 in a manner such that the path of light from each LED to the detector 38 is substantially the same distance. In addition, the path must traverse a portion of the patient's body through which a usable amount of light is passed, for example, a finger, toe, earlobe, or the nasal septum. Because changes in the lightpath can significantly affect the readings taken, as noted above, the sensor must maintain the position of LEDs 40 and 42 and detector 38 with respect to the transmission path through the patient's skin at all times. Otherwise, signal fluctuations known as motion-artifact may be produced. In addition, the sensor should apply only insubstantial presssure to the patient's skin. Otherwise, normal arterial blood flow upon which the pulse oximeter relies for accurate operation, may be disrupted. Finally, the sensor should be quickly attachable to the patient and should cause no discomfort.

Figure 12:
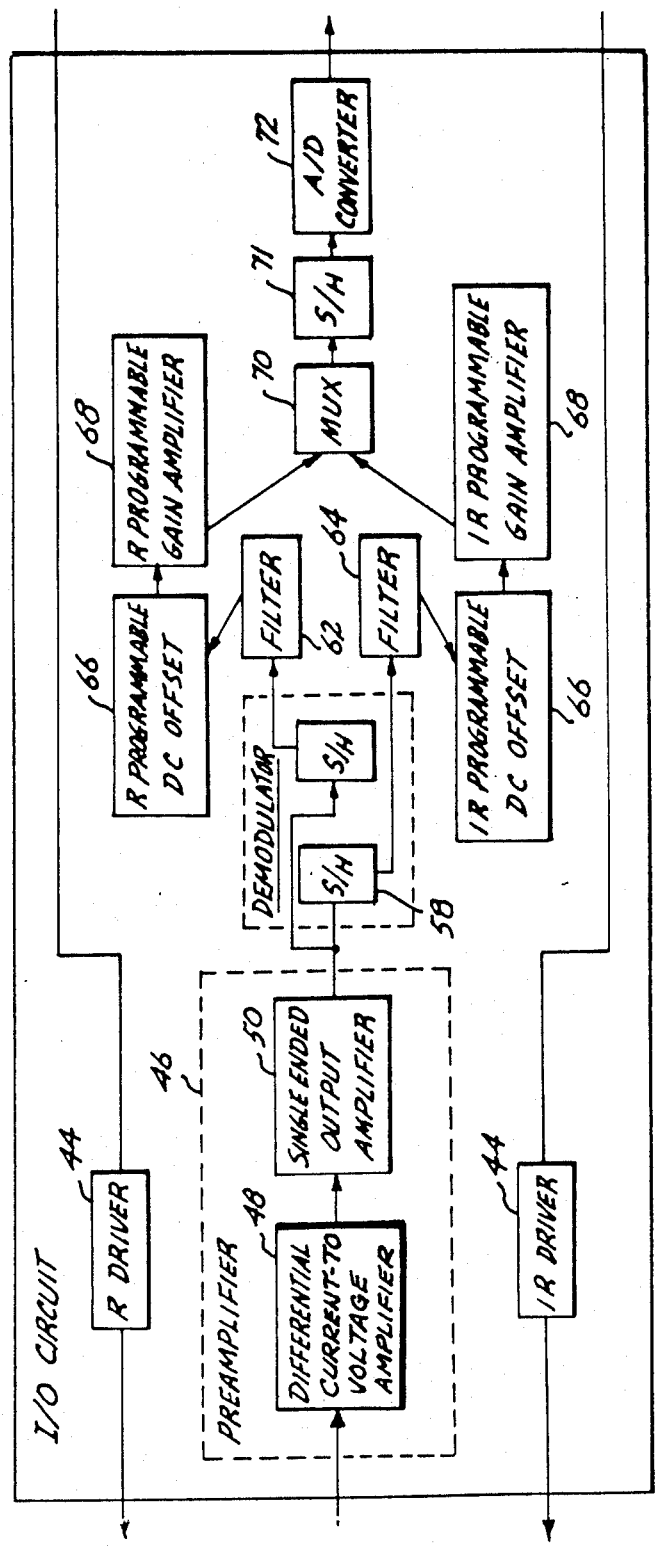
FIG. 12 is a more detailed schematic of the I/O circuit illustrated in the system of FIG. 1.

LEDs 40 and 42 are supplied with current by transistor drivers 44 located in the I/O circuit 14, as shown in FIG. 12. Drivers 44 are controlled by microcomputer 16 to produce current pulses at a 960 Hz repetition rate. The duration of each pulse is 70 microseconds and a pulse is supplied to the red wavelength LED 40 first and then to the infrared wavelength LED 42. The voltage drop across scaling resistors in the drivers 44 allows the magnitude of the current pulses to be determined and, thus, maintained in a manner described in greater detail below. LEDs 40 and 42 respond to the current pulses by producing corresponding light pulses transmitted through the finger to detector 38. Detector 38, in turn, produces a signal that includes information about the pulsatile response of the finger to the red and infrared wavelength light, intermixed at the 960 Hz LED pulse repetition rate.

In a preferred embodiment of the invention, a red optical filter 45 interrupts the lightpath between the LEDs 40 and 42 and the detector 38, as shown in FIG. 9. Preferably, filter 45 is a Kodak No. 29 wratten gel filter. Its function is to eliminate the influence of fluorescent light flicker on the oxygen saturation determination made. As will be appreciated, although the body of sensor 12 may be made on an opaque material that blocks a significant portion of the ambient light, some ambient light may still reach detector 38. Light from the sun and incandescent lamps is substantially continuous. Fluorescent lighting, on the other hand, includes alternating energized and deenergized intervals that form a visually imperceptible flicker. The frequency of the fluorescent light flicker is such that it might influence the signal produced by detector 38 in response to light received from LED 40 at the red wavelength. Thus, the red optical filter 45 is placed over the detector 38 and filters out any fluorescent light present, eliminating the effect its flicker might have on the oxygen saturation determination made.

Figure 13:
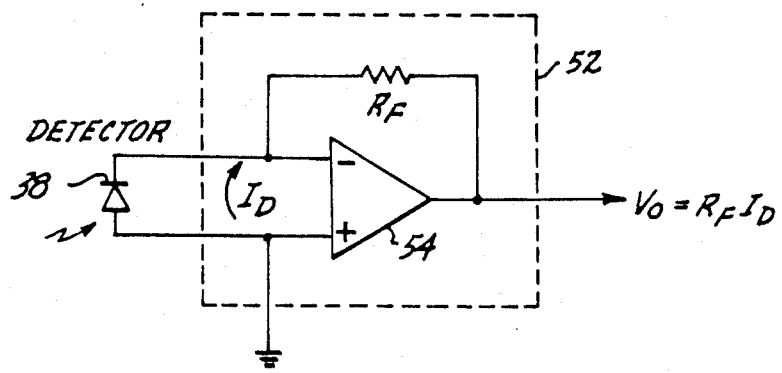
FIG. 13 is a schematic diagram of a conventional current-to-voltage amplifier circuit.

At the I/O circuit 14, the signal from detector 38 is received by a preamplifier 46. In a preferred embodiment, preamplifier 46 includes a current-to-voltage transimpedance amplifier 48 and a single-ended output amplifier 50. To understand the advantages of using the differential current-to-voltage amplifier 48, it may first be helpful to consider the operation of a transimpedance amplifier as shown in FIG. 13. As shown, a transimpedance amplifier 52 is substantially comprised of an operational amplifier 54 and gain determination resistor $R_F$. With a detector 38 connected to the inputs of the amplifier as shown, a current $I_D$ is input to the amplifier upon the detection of suitable wavelength light. The output of ampifier 52 is designated $V_0$ and, as will be appreciated, is equal to the product of the detector current $I_D$ and the gain determination resistor $R_F$. The primary problem with such a construction is that it also amplifies the external interference noise produced, making the signal extracted less accurate.

Figure 14:
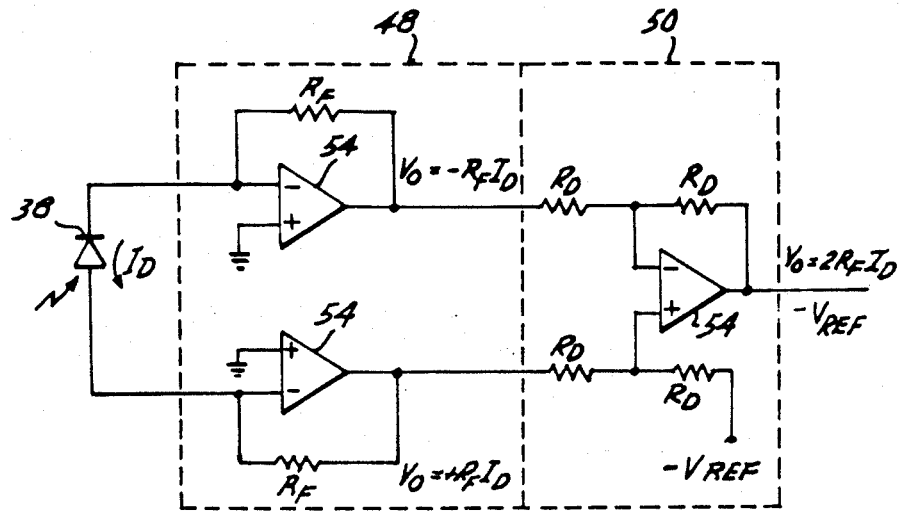
FIG. 14 is a schematic diagram of a differential, current-to-voltage preamplifier circuit included in the I/O circuit of FIG. 1.

Adoption of the differential current-to-voltage amplifier 48, when combined with the single-ended output amplifier 50 as shown in FIG. 14, however, eliminates this problem. As shown, the differential transimpedance amplifier 48 produces positive and negative versions of the output, the absolute value of each version being equal to the product of the gain determination resistance $R_F$ and the detector current $I_D$. These outputs are then supplied to the single-ended output amp 50, which provides unity gain, thus producing an output signal having a magnitude that is twice that of the inputs. An advantage of this arrangement is that external interference noise is cancelled at the single-ended output amplifier 50 by the opposing signs of the two differential transimpedance amplifier outputs. In addition, twice the signal is produced with the current noise only increasing by a magnitude of 1.414. Therefore, an improved signal-to-noise ratio results.

At this point, the mixed signal indicative of the red and infrared wavelength responses of detector 38 has been amplified and is input to a demodulator 56 to extract the red pulsatile and infrared pulsatile waveforms shown in FIGS. 10 and 11. In a preferred arrangement, the demodulator 56 includes a sample-and-hold (S/H) circuit 58 that responds to the detector signal produced in response to red wavelength light and a sample-and-hold (S/H) circuit 60 that responds to the infrared wavelength response of detector 38. The timing of circuits 58 and 60 is controlled so that each circuit samples the signal input to demodulator 56 during the portion of the signal corresponding to the wavelength to which it responds. In this manner, two signals are reconstructed from the single input to demodulator 56. As noted above, these signals correspond to the red pulsatile signal and infrared pulsatile signals shown in FIGS. 10 and 11.

To remove high-frequency noise from the outputs of circuits 58 and 60, they are input to lowpass filters 64 and 62. In a preferred embodiment, the "red" lowpass filter 62 and "infrared" lowpass filter 64 each incude two stages. The first stage of each filter utilizes a fifth-order, monolithic integrated circuit switched capacitor filter because of its low-cost and relatively small physical size. Since both the "red" and "infrared" signals pass through identical first-stage filters, their gain and phase frequency responses are matched. The second stage of each filter is a second-order Bessel filter having a slightly higher rolloff frequency than the first stage. This insures that the first-stage filter is the dominant filter of the two-stage combination, producing the desired filtering accuracy. The second stage then filters the switching noise from the first-stage output.

The filtered red and infrared pulsatile signals are next prepared for conversion and transmission to the microcomputer 16. As will be discussed in greater detail below, this process involves the use of a programmable DC subtractor or offset 66 followed by a programmable gain amplifier 68 having a gain range from approximately one to 256. The appropriately processed signals are combined at multiplexer 70, sampled and held, and converted to digital form by A/D converter 72 for transmission to microcomputer 16.

Before a more complete discussion of the operation of programmable subtractor 66, programmable gain amplifier 68, multiplier 70 and A/D converter 72 is provided, several details regarding the signals to be transferred to microcomputer 16 should be noted. For example, as shown in FIGS. 10 and 11, the signal produced by detector 30 in response to light at each wavelength includes components that, for convenience, are termed baseline and pulsatile. The baseline component approximates the intensity of light received at detector 38 when only the "fixed" nonpulsatile absorptive component is present in the finger. This component of the signal is relatively constant over short intervals but does vary with nonpulsatile physiological changes or system changes, such as movement of probe 12 on the finger. Over a relatively long interval this baseline component may vary significantly. As will be appreciated, the magnitude of the baseline component at a given point in time is substantially equal to the level identified in FIG. 10 as $R_H$. For convenience, however, the baseline component may be thought of as the level indicated by $R_L$, with the pulsatile component varying between the values for $R_H$ and $R_L$ over a given pulse. That pulsatile component is attributable to light transmission changes through the finger resulting from blood volume changes in the finger during a pulse as well as oxygen saturation concentration fluctuations. Typically, the pulsatile component may be relatively small in comparison to the baseline component and is shown out of proportion in FIGS. 10 and 11.

Because the baseline signal does not directly convey information relating to oxygen saturation or pulse, the pulsatile signal is primarily of interest. As will be readily appreciated, if the entire signal shown in FIGS. 10 and 11, including the AC and DC components, was amplified and converted to a digital format for use by microcomputer 16, a great deal of the accuracy of the conversion would be wasted because a substantial portion of the resolution would be used to break down the baseline component. For example, with an A/D converter employed having an input range of between +10 and −10 volts, a signal having a baseline component that is four times that of the pulsatile component can be amplified until the baseline component is represented by a 16-volt difference and the pulsatile signal represented by a 4-volt difference. With a 12-bit A/D converter 72, the total signal can be resolved into 4096 components. Therefore, the number of incremental levels representing the pulsatile signal would be approximately 820. If, on the other hand, the baseline component is removed prior to the conversion, the pulsatile signal could be resolved into 4096 intervals, substantially improving accuracy.

The disclosed invention employs this technique, as the first half of a construction-reconstruction process controlled by microcomputer 16. Accordingly, an input signal received from each filter 62 and 64 includes the entire transmission signal. The programmable subtractors 66 remove a substantial offset portion of the total signal of each waveform and the programmable gain amplifiers 68 gain-up the remaining signal for conversion by A/D converter 72. A digital reconstruction of the original signal is then produced by the microcomputer, which through the use of digital feedback information, removes the gain and adds the offset voltages back to the signal.

Feedback from microcomputer 16 to I/O circuit 14 is also required to maintain the values for the offset voltage, gain, and driver currents at levels appropriate to produce optimal A/D converter 72 resolution. Proper control requires that the microcomputer continually analyze, and respond to, the offset voltage, gain, driver currents and the output of A/D converter in a manner to be described next.

Briefly, with reference to FIG. 15, thresholds L1 and L2 slightly below and above the maximum positive and negative excursions L3 and L4 allowable for the A/D converter 72 input, are established and monitored by microcomputer 16 at the A/D converter 72 output. When the magnitude of the signal input to, and output from, A/D converter 72 exceeds either of the thresholds L1 or L2, the driver currents $I_D$, are readjusted to decrease the intensity of light impinging upon the detector 38. In this manner, the A/D converter 72 is not overdriven and the margin between L1 and L3 and between L2 and L4 helps assure this even for rapidly varying signals. An operable voltage margin for A/D converter 72 exists outside of the thresholds, allowing A/D converter 72 to continue operating while the appropriate feedback adjustments to A and $V_{OS}$ are made.

When the signal from A/D converter 72 exceeds positive and negative thresholds L5 or L6, microcomputer 16 responds by signaling the programmable subtractor 66 to increase the offset voltage being subtracted. This is done through the formation and transmission of an offset code whose magnitude is dependent upon the level of the signal received from converter 72.

Figure 15:
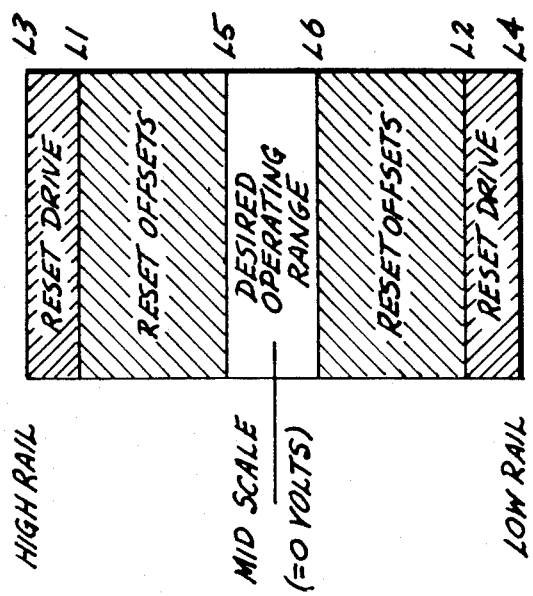
FIG. 15 is a graphical representation of the possible ranges of the I/O circuit output showing the desired response of the I/O circuit and microcomputer at each of the various possible ranges.

Three different gain adjustments are employed in the arrangement graphically depicted in FIG. 15. For example, if microcomputer 16 determines that the A/D converter 72 signal has not exceeded positive and negative thresholds L7 and L8, the current value of a gain code is increased. This revised gain code is then transmitted to the programmable amplifier 68, which makes the appropriate adjustment to the gain A. If the A/D converter signal exceeds positive and negative thresholds L9 and L10, the gain code is adjusted downward as a function of the signal magnitude. Similarly, if separate lower positive and negative thresholds L11 and L12 are exceeded, the gain code is also adjusted downward as a separate function of the signal magnitude.

The manner in which the various thresholds are established and the relationship of the gain and offset codes to the signal received can be altered to produce substantially any form of control desired. Thus, the arrangement shown in FIG. 15 is illustrative only and represents the currently preferred embodiment.

Figure 16:
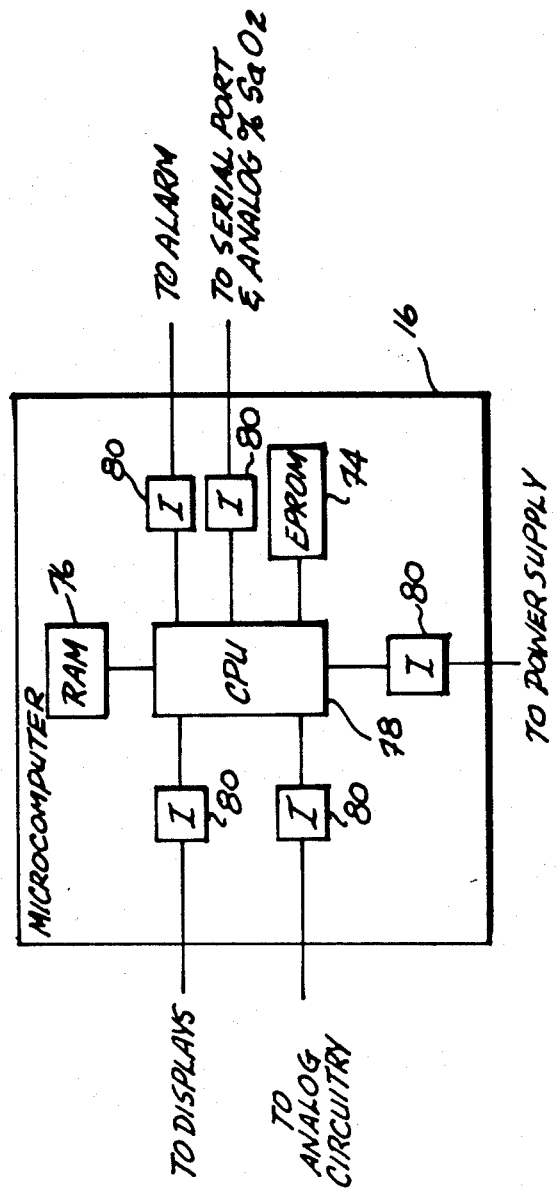
FIG. 16 is a more complete schematic diagram of the microcomputer illustrated in FIG. 1.

As will be appreciated from FIG. 16, the instructions for the microcomputer program that controls the signal construction-reconstruction discussed above are stored in erasable, programmable, read-only memory (EPROM) 74 of microcomputer 16. Similarly, values for $V_H$, $V_L$, $\Delta V$, $\Delta ts$ and $\Delta tp$ at wavelengths $\lambda_1$ and $\lambda_2$ are determined pursuant to peak-detection software contained in EPROM 74. These values are stored in random-access memory (RAM) 76 for operation upon by a central processing unit (CPU) 78 in accordance with further computational instructions stored in EPROM 74. Interfaces 80 act as input and output buffers for microcomputer 16.

The computational software in EPROM 74 initially causes CPU 78 to determine the present value for $R_{OS}$ by substituting the measured values for $V_H$, $V_L$, $\Delta V$, $\Delta ts$ and $\Delta tp$ at wavelengths $\lambda_1$ and $\lambda_2$ into equation (73):

$$R_{OS} = \frac{\ln\left[\frac{V_H}{V_L - (\Delta ts \Delta V / \Delta tp)}\right] @ \lambda_1}{\ln\left[\frac{V_H}{V_L - (\Delta ts \Delta V / \Delta tp)}\right] @ \lambda_2} \quad (83)$$

Then, the computational software instructs CPU 78 to determine the oxygen saturation from $R_{OS}$ by use of a calibration curve, such as the one depicted in FIG. 7. The calibration curve is a plot of the relationship between independently determined oxygen saturations corresponding to values of $R_{OS}$ produced by oximeter 10 in accordance with the technique described above.

With sufficiently large space in EPROM 74, enough points along the calibration curve can be stored in a look-up table to allow CPU 78 to extract an accurate indication of oxygen saturation from the value of $R_{OS}$ input to EPROM 74. The storage of a sufficient number of calibration curve data points may, however, necessitate the use of an undesirably large capacity EPROM 74. For that reason, a second method of storing the calibration curve information is preferred.

Pursuant to that method, independently derived data associating $R_{OS}$ with the oxygen saturation is obtained, a mathematical expression between the two can be derived from a plot of the curve. The basic formula and the coefficients of the formula's variables are then stored in EPROM 74. When a value for $R_{OS}$ is measured, CPU 78 extracts the coefficients from EPROM 74 and computes a value for the oxygen saturation. This technique allows information completely identifying the entire calibration curve, or a family of such curves, to be stored within a relatively small amount of EPROM 74 space.

The computational software in EPROM 74 also instructs CPU 78 to determine the pulse rate from the signal period tp. Displays 20 then provide visible and audible outputs of the oxygen saturation and pulse rate in a manner conveniently used by the operator of oximeter 10.

While the references have been described with reference to a preferred embodiment, it is to be clearly understood by those skilled in the art that the invention is not limited thereto, and that the scope of the invention is to be interpreted only in conjunction with the following claims.

The embodiments of the invention in which an exclusive property or privilege is claimed are defined as follows:

1. An apparatus for determining the oxygen saturation of arterial blood flowing in tissue that is illuminated with light at two wavelengths, the light being received upon emergence from the tissue by detection means that produces signals that are proportional to the intensity of the light received at each of the wavelengths, the intensity of light received being a function of at least one time-dependent absorption coefficient, said apparatus comprising:
   sampling means for determining the magnitude of said signals at a plurality of sample times spaced over an interval greater than the period of one pulse as exhibited by said arterial blood flowing in said tissue; and
   processing means for producing a single indication of said oxygen saturation that is corrected for any time-dependent variation in said absorption coefficient from said sample times and the magnitudes of said signals at said sample times.

2. The apparatus of claim 1, wherein said processing means produces said single indication of said oxygen saturation in accordance with the relationship:

$$R_{OS} = \frac{\ln(T_1/T_0) - m\ln(T_3/T_1) \ @ \ \lambda_1}{\ln(T_1/T_0) - m\ln(T_3/T_1) \ @ \ \lambda_2}$$

where
   $R_{OS}$ = said single indication of said oxygen saturation produced;
   $\lambda_1$ = the first of said two wavelengths of said transilluminating light;
   $\lambda_2$ = the second of said two wavelengths of said transilluminating light;
   $T_0$ = the magnitude of the signal at the diastole of a first pulse exhibited by said arterial blood flowing in said tissue, for the wavelength indicated;
   $T_1$ = the magnitude of the signal at the systole of the first pulse, for the wavelength indicated;
   $T_3$ = the magnitude of the signal at the systole of a second pulse, for the wavelength indicated; and
   $m$ = the ratio of the time between an adjacent diastole and systole to the time between adjacent diastoles.

3. The apparatus of claim 1, wherein said processing means produces said single indication of said oxygen saturation in accordance with the relationship:

$$R_{OS} = \frac{\ln\left[\dfrac{V_H}{V_L - (\Delta ts \Delta V/\Delta tp)}\right] @ \lambda_1}{\ln\left[\dfrac{V_H}{V_L - (\Delta ts \Delta V/\Delta tp)}\right] @ \lambda_2}$$

where
- $R_{OS}$ = said single indication of said oxygen saturation produced;
- $\lambda_1$ = the first of said two wavelengths of said transilluminating light;
- $\lambda_2$ = the second of said two wavelengths of said transilluminating light;
- $V_H$ = the magnitude of said signal at the diastole of a second pulse exhibited by said arterial blood flowing in said tissue, for the wavelength indicated;
- $V_L$ = the magnitude of said signal at the systole of said second pulse, for the wavelength indicated;
- $\Delta V$ = the difference in the magnitude of said signal between said systole of said second pulse and said systole of a first pulse, for the wavelength indicated;
- $\Delta ts$ = the difference in time between the systole and diastole of one of said first and second pulses, as measured from said signal corresponding to the wavelength indicated; and
- $\Delta tp$ = the period of said pulse, as measured from said signal corresponding to the wavelength indicated.

4. The apparatus of claim 1, wherein said processing means produces said single indication of said oxygen saturation in accordance with the relationship:

$$R_{OS} = \frac{\ln\left[\dfrac{V_H}{V_L}\left(\dfrac{V_L + \Delta V(\Delta ts/\Delta tp)}{V_L}\right)\right] @ \lambda_1}{\ln\left[\dfrac{V_H}{V_L}\left(\dfrac{V_L + \Delta V(\Delta ts/\Delta tp)}{V_L}\right)\right] @ \lambda_2}$$

where
- $R_{OS}$ = said single indication of said oxygen saturation produced;
- $\lambda_1$ = the first of said two wavelengths of said transilluminating light;
- $\lambda_2$ = the second of said two wavelengths of said transilluminating light;
- $V_H$ = the magnitude of said signal at the diastole of a second pulse exhibited by said arterial blood flowing in said tissue, for the wavelength indicated;
- $V_L$ = the magnitude of said signal at the systole of said second pulse, for the wavelength indicated;
- $\Delta V$ = the difference in the magnitude of said signal between said systole of said second pulse and said systole of a first pulse, for the wavelength indicated;
- $\Delta ts$ = the difference in time between the systole and diastole of one of said first and second pulses, as measured from said signal corresponding to the wavelength indicated; and
- $\Delta tp$ = the period of said pulse, as measured from said signal corresponding to the wavelength indicated.

5. The apparatus of claim 1, wherein said processing means produces said single indication of said oxygen saturation in accordance with the relationship:

$$R_{OS} = \frac{\ln[(V_H/V_L)(1 + (\Delta ts/\Delta tp)(\Delta V/V_L))] @ \lambda_1}{\ln[(V_H/V_L)(1 + (\Delta ts/\Delta tp)(\Delta V/V_L))] @ \lambda_2}$$

where
- $R_{OS}$ = said single indication of said oxygen saturation produced;
- $\lambda_1$ = the first of said two wavelengths of said transilluminating light;
- $\lambda_2$ = the second of said two wavelengths of said transilluminating light;
- $V_H$ = the magnitude of said signal at the diastole of a second pulse exhibited by said arterial blood flowing in said tissue, for the wavelength indicated;
- $V_L$ = the magnitude of said signal at the systole of said second pulse, for the wavelength indicated;
- $\Delta V$ = the difference in the magnitude of said signal between said systole of said second pulse and said systole of a first pulse, for the wavelength indicated;
- $\Delta ts$ = the difference in time between the systole and diastole of one of said first and second pulses, as measured from said signal corresponding to the wavelength indicated; and
- $\Delta tp$ = the period of said pulse, as measured from said signal corresponding to the wavelength indicated.

6. The apparatus of claim 1, wherein said processing means produces said single indication of said oxygen saturation in accordance with the relationship:

$$R_{OS} = \frac{\ln[T_0/T_1(1 + (m/2)(T_2/T_0 - 1) + (m/2)(T_3/T_1 - 1))] @ \lambda_1}{\ln[T_0/T_1(1 + (m/2)(T_2/T_0 - 1) + (m/2)(T_3/T_1 - 1))] @ \lambda_2}$$

where
- $R_{OS}$ = said single indication of said oxygen saturation produced;
- $\lambda_1$ = the first of said two wavelengths of said transilluminating light;
- $\lambda_2$ = the second of said two wavelengths of said transilluminating light;
- $T_0$ = the magnitude of the signal at the diastole of a first pulse exhibited by said arterial blood flowing in said tissue, for the wavelength indicated;
- $T_1$ = the magnitude of the signal at the systole of the first pulse, for the wavelength indicated;
- $T_3$ = the magnitude of the signal at the systole of a second pulse, for the wavelength indicated; and
- $m$ = the ratio of the time between an adjacent diastole and systole to the time between adjacent diastoles.

7. The apparatus of claim 1, wherein said processing means produces said single indication of said oxygen saturation in accordance with the relationship:

$$R_{OS} = \frac{\ln\left[T_2/T_3\left(1 + \sum_{i,j,k} m_k(T_i/T_j - 1)\right)\right] @ \lambda_1}{\ln\left[T_2/T_3\left(1 + \sum_{i,j,k} m_k(T_i/T_j - 1)\right)\right] @ \lambda_2}$$

where
- $R_{OS}$ = said single indication of said oxygen saturation produced;
- $\lambda_1$ = the first of said two wavelengths of said transilluminating light;

$\lambda_2$ = the second of said two wavelengths of said transilluminating light;

$T_2$ = the magnitude of the signal at the diastole of a second pulse exhibited by said arterial blood flowing in said tissue, for the wavelength indicated;

$T_3$ = the magnitude of the signal at the systole of a second pulse, for the wavelength indicated; and $T_i$ = the magnitude of the signal at a time $t_i$, for the wavelength indicated;

$T_j$ = the magnitude of the signal at a time $t_j$, for the wavelength indicated;

$m_k$ = the ratio of the time between an adjacent diastole and systole to the time between adjacent diastoles; and i, j, and k = positive and negative integers.

8. The apparatus of claim 1, wherein said processing means produces said single indication of said oxygen saturation in accordance with the relationship:

$$R_{OS} = \frac{\ln[T_0/T_1] + \frac{1}{2}[\ln(P_1(t_1)/P_1(t_0)) + \ln(P_0(t_1)/P_0(t_0))] \quad @ \, \lambda_1}{\ln[T_0/T_1] + \frac{1}{2}[\ln(P_1(t_1)/P_1(t_0)) + \ln(P_0(t_1)/P_0(t_0))] \quad @ \, \lambda_2}$$

where:
$R_{OS}$ = said single indication of said oxygen saturation produced;
$\lambda_1$ = the first of said two wavelengths of said transilluminating light;
$\lambda_2$ = the second of said two wavelengths of said transilluminating light;
$T_0$ = the magnitude of the signal at the diastole of a first pulse exhibited by said arterial blood flowing in said tissue, for the wavelength indicated;
$T_1$ = the magnitude of the signal at the systole of the first pulse, for the wavelength indicated;
$P_0(t)$ = a first interpolating function indicative of a time-varying characteristic of said tissue;
$P_1(t)$ = a second interpolating function indicative of a time-varying characteristic of said tissue and said arterial blood;
$t_0$ = a first point in time used to identify corresponding points on said signals; and
$t_1$ = a second point in time used to identify corresponding points on said signals.

9. The apparatus of claim 1, further comprising means for comparing the indication produced by said processing means with independently derived oxygen saturation curves to further indicate said oxygen saturation of said arterial blood in said tissue.

10. The apparatus of claim 9, further comprising means for producing an output representative of said oxygen saturation indicated.

11. The oximeter of claim 1, further comprising a differential current-to-voltage amplifier for amplifying said signals produced by said detection means before the magnitude of said signals is determined by said sampling means.

12. An oximeter, comprising:
a light source for exposing tissue having arterial blood flowing therein to light at two wavelengths;
detection means, responsive to the exposure of said tissue to said light, for producing signals that are proportional to the intensity of said light received at each of said wavelengths, the intensity of light received being a function of at least one time-dependent absorption coefficient, said signals containing information about the oxygen saturation of said arterial blood;

sampling means for determining the magnitude of said signals at a plurality of sample times spaced over an interval greater than the period of one pulse as exhibited by said arterial blood flowing in said tissue; and processing means for producing a single indication of said oxygen saturation that is corrected for any time-dependent variation in said absorption coefficient from said sample times and the magnitudes of said signals at said sample times.

13. The oximeter of claim 12, wherein said processing means produces said single indication in accordance with the relationship:

$$R_{OS} = \frac{\ln(T_1/T_0) - m\ln(T_3/T_1) \quad @ \, \lambda_1}{\ln(T_1/T_0) - m\ln(T_3/T_1) \quad @ \, \lambda_2}$$

where
$R_{OS}$ = said single indication of said oxygen saturation produced;
$\lambda_1$ = the first of said two wavelengths of said transilluminating light;
$\lambda_2$ = the second of said two wavelengths of said transilluminating light;
$T_0$ = the magnitude of the signal at the diastole of a first pulse exhibited by said arterial blood flowing in said tissue, for the wavelength indicated;
$T_1$ = the magnitude of the signal at the systole of the first pulse, for the wavelength indicated;
$T_3$ = the magnitude of the signal at the systole of a second pulse, for the wavelength indicated; and
m = the ratio of the time between an adjacent diastole and systole to the time between adjacent diastoles.

14. The oximeter of claim 12, wherein said processing means produces said single indication of said oxygen saturation in accordance with the relationship:

$$R_{OS} = \frac{\ln\left[\frac{V_H}{V_L - (\Delta ts \Delta V/\Delta tp)}\right] @ \, \lambda_1}{\ln\left[\frac{V_H}{V_L - (\Delta ts \Delta V/\Delta tp)}\right] @ \, \lambda_2}$$

where
$R_{OS}$ = said single indication of said oxygen saturation produced;
$\lambda_1$ = the first of said two wavelengths of said transilluminating light;
$\lambda_2$ = the second of said two wavelengths of said transilluminating light;
$V_H$ = the magnitude of said signal at the diastole of a second pulse exhibited by said arterial blood flowing in said tissue, for the wavelength indicated;
$V_L$ = the magnitude of said signal at the systole of said second pulse, for the wavelength indicated;
$\Delta V$ = the difference in the magnitude of said signal between said systole of said second pulse and said systole of a first pulse, for the wavelength indicated;
$\Delta ts$ = the difference in time between the systole and diastole of one of said first and second pulses, as measured from said signal corresponding to the wavelength indicated; and
$\Delta tp$ = the period of said pulse, as measured from said signal corresponding to the wavelength indicated.

15. The oximeter of claim 12, wherein said two wavelengths comprise red and infrared wavelengths.

16. The oximeter of claim 15, further comprising a red optical filter for filtering said light received by said detection means.

17. The oximeter of claim 12, further comprising a differential current-to-voltage amplifier for amplifying said signals produced by said detection means before the magnitude of said signals is determined by said sampling means.

18. A method of determining the oxygen saturation of arterial blood flowing in tissue that is illuminated with light at two wavelengths, the light being received upon emergence from the tissue by detection means that produces signals that are proportional to the intensity of the light received at each of the wavelengths, the intensity of light received being a function of at least one time-dependent absorption coefficient, said method comprising the steps of:
storing the magnitude of said signals at a plurality of sample times spaced over an interval greater than the period of one pulse as exhibited by said arterial blood flowing in said tissue; and
producing a single indication of said oxygen saturation of said arterial blood that is corrected for any time-dependent variation in said absorption coefficient from said sample times and the magnitudes of said signals at said sample times.

19. The method of claim 18, wherein said single indication of said oxygen saturation is produced in accordance with the relationship:

$$R_{OS} = \frac{\ln(T_1/T_0) - m\ln(T_3/T_1) \ @ \ \lambda_1}{\ln(T_1/T_0) - m\ln(T_3/T_1) \ @ \ \lambda_2}$$

where
$R_{OS}$ = said single indication of said oxygen saturation produced;
$\lambda_1$ = the first of said two wavelengths of said transilluminating light;
$\lambda_2$ = the second of said two wavelengths of said transilluminating light;
$T_0$ = the magnitude of the signal at the diastole of a first pulse exhibited by said arterial blood flowing in said tissue, for the wavelength indicated;
$T_1$ = the magnitude of the signal at the systole of the first pulse, for the wavelength indicated;
$T_3$ = the magnitude of the signal at the systole of a second pulse, for the wavelength indicated; and
m = the ratio of the time between an adjacent diastole and systole to the time between adjacent diastoles.

20. The method of claim 18, wherein said single indication of said oxygen saturation is produced in accordance with the relationship:

$$R_{OS} = \frac{\ln\left[\frac{V_H}{V_L - (\Delta t s \Delta V/\Delta t p)}\right] @ \lambda_1}{\ln\left[\frac{V_H}{V_L - (\Delta t s \Delta V/\Delta t p)}\right] @ \lambda_2}$$

where
$R_{OS}$ = said single indication of said oxygen saturation produced;
$\lambda_1$ = the first of said two wavelengths of said transilluminating light;
$\lambda_2$ = the second of said two wavelengths of said transilluminating light;
$V_H$ = the magnitude of said signal at the diastole of a second pulse exhibited by said arterial blood flowing in said tissue, for the wavelength indicated;
$V_L$ = the magnitude of said signal at the systole of said second pulse, for the wavelength indicated;
$\Delta V$ = the difference in the magnitude of said signal between said systole of said second pulse and said systole of a first pulse, for the wavelength indicated;
$\Delta t s$ = the difference in time between the systole and diastole of one of said first and second pulses, as measured from said signal corresponding to the wavelength indicated; and
$\Delta t p$ = the period of said pulse, as measured from said signal corresponding to the wavelength indicated.

21. The method of claim 18, wherein said single indication of said oxygen saturation is produced in accordance with the relationship:

$$R_{OS} = \frac{\ln\left[\frac{V_H}{V_L}\left(\frac{V_L + \Delta V(\Delta t s/\Delta t p)}{V_L}\right)\right] @ \lambda_1}{\ln\left[\frac{V_H}{V_L}\left(\frac{V_L + \Delta V(\Delta t s/\Delta t p)}{V_L}\right)\right] @ \lambda_2}$$

where:
$R_{OS}$ = said single indication of said oxygen saturation produced;
$\lambda_1$ = the first of said two wavelengths of said transilluminating light;
$\lambda_2$ = the second of said two wavelengths of said transilluminating light;
$V_H$ = the magnitude of said signal at the diastole of a second pulse exhibited by said arterial blood flowing in said tissue, for the wavelength indicated;
$V_L$ = the magnitude of said signal at the systole of said second pulse, for the wavelength indicated;
$\Delta V$ = the difference in the magnitude of said signal between the systole of said second pulse and the systole of a first pulse, for the wavelength indicated;
$\Delta t s$ = the difference in time between the systole and diastole of one of said first and second pulses, as measured from said signal corresponding to the wavelength indicated; and
$\Delta t p$ = the period of said pulse, as measured from said signal corresponding to the wavelength indicated.

22. The method of claim 18, wherein said single indication of said oxygen saturation is produced in accordance with the relationship:

$$R_{OS} = \frac{\ln[(V_H/V_L)(1 + (\Delta t s/\Delta t p)(\Delta V/V_L))] \ @ \ \lambda_1}{\ln[(V_H/V_L)(1 + (\Delta t s/\Delta t p)(\Delta V/V_L))] \ @ \ \lambda_2}$$

where
$R_{OS}$ = said single indication of said oxygen saturation produced;
$\lambda_1$ = the first of said two wavelengths of said transilluminating light;
$\lambda_2$ = the second of said two wavelengths of said transilluminating light;
$V_H$ = the magnitude of said signal at the diastole of a second pulse exhibited by said arterial blood flowing in said tissue, for the wavelength indicated;

$V_L$ = the magnitude of said signal at the systole of said second pulse, for the wavelength indicated;

$\Delta V$ = the difference in the magnitude of said signal between said systole of said second pulse and said systole of a first pulse, for the wavelength indicated;

$\Delta ts$ = the difference in time between the systole and diastole of one of said first and second pulses, as measured from said signal corresponding to the wavelength indicated; and $\Delta tp$ = the period of said pulse, as measured from said signal corresponding to the wavelength indicated.

23. The method of claim 18, wherein said single indication of said oxygen saturation is produced in accordance with the relationship:

$$R_{OS} = \frac{\ln[T_0/T_1(1 + (m/2)(T_2/T_0 - 1) + (m/2)(T_3/T_1 - 1))] \quad @ \lambda_1}{\ln[T_0/T_1(1 + (m/2)(T_2/T_0 - 1) + (m/2)(T_3/T_1 - 1))] \quad @ \lambda_2}$$

where $R_{OS}$ = said single indication of said oxygen saturation produced;

$\lambda_1$ = the first of said two wavelengths of said transilluminating light;

$\lambda_2$ = the second of said two wavelengths of said transilluminating light;

$T_0$ = the magnitude of the signal at the diastole of a first pulse exhibited by said arterial blood flowing in said tissue, for the wavelength indicated;

$T_1$ = the magnitude of the signal at the systole of the first pulse, for the wavelength indicated;

$T_3$ = the magnitude of the signal at the systole of a second pulse pulse, for the wavelength indicated; and $m$ = the ratio of the time between an adjacent diastole and systole to the time between adjacent diastoles.

24. The method of claim 18, wherein said single indication of said oxygen saturation is produced in accordance with the relationship:

$$R_{OS} = \frac{\ln\left[T_2/T_3\left(1 + \sum_{i,j,k} m_k(T_i/T_j - 1)\right)\right] \quad @ \lambda_1}{\ln\left[T_2/T_3\left(1 + \sum_{i,j,k} m_k(T_i/T_j - 1)\right)\right] \quad @ \lambda_2}$$

where $R_{OS}$ = said single indication of said oxygen saturation produced;

$\lambda_1$ = the first of said two wavelengths of said transilluminating light;

$\lambda_2$ = the second of said two wavelengths of said transilluminating light;

$T_2$ = the magnitude of the signal at the diastole of a second pulse exhibited by said arterial blood flowing in said tissue, for the wavelength indicated;

$T_3$ = the magnitude of the signal at the systole of a second pulse, for the wavelength indicated; and $T_i$ = the magnitude of the signal at a time $t_i$, for the wavelength indicated;

$T_j$ = the magnitude of the signal at a time $t_j$, for the wavelength indicated;

$m_k$ = the ratio of the time between an adjacent diastole and systole to the time between adjacent diastoles; and $i$, $j$, and $k$ = positive and negative integers.

25. The method of claim 18, wherein said single indication of said oxygen saturation is produced in accordance with the relationship:

$$R_{OS} = \frac{\ln[T_0/T_1) + \frac{1}{2}[\ln(P_1(t_1)/P_1(t_0)) + \ln(P_0(t_1)/P_0(t_0))] \quad @ \lambda_1}{\ln[T_0/T_1) + \frac{1}{2}[\ln(P_1(t_1)/P_1(t_0)) + \ln(P_0(t_1)/P_0(t_0))] \quad @ \lambda_2}$$

where:

$R_{OS}$ = said single indication of said oxygen saturation produced;

$\lambda_1$ = the first of said two wavelengths of said transilluminating light;

$\lambda_2$ = the second of said two wavelengths of said transilluminating light;

$T_0$ = the magnitude of the signal at the diastole of a first pulse exhibited by said arterial blood flowing in said tissue, for the wavelength indicated;

$T_1$ = the magnitude of the signal at the systole of the first pulse, for the wavelength indicated;

$P_0(t)$ = a first interpolating function indicative of a time-varying characteristic of said tissue;

$P_1(t)$ = a second interpolating function indicative of a time-varying characteristic of said tissue and said arterial blood;

$t_0$ = a first point in time used to identify corresponding points on said signals; and $t_1$ = a second point in time used to identify corresponding points on said signals.

26. The method of claim 18, further comprising the step of comparing the indication produced by the processing of said sample times and said magnitudes with independently derived oxygen saturation curves to further indicate said oxygen saturation of said arterial blood in said tissue.

27. The method of claim 26, further comprising the step of producing an output representative of said oxygen saturation determined.

28. The method of claim 18, wherein the intensity of light received is a function of a first time-dependent absorption coefficient characteristic of said arterial blood flowing in said tissue and a second time-dependent absorption coefficient characteristic of, in part, said tissue.

29. The method of claim 28, wherein said single indication of said oxygen saturation of said arterial blood is determined in accordance with a relationship including at least one uncorrected term and at least one corrective term.

* * * * *

UNITED STATES PATENT AND TRADEMARK OFFICE
CERTIFICATE OF CORRECTION

PATENT NO. : 4,859,056
DATED : August 22, 1989
INVENTOR(S) : Stephen J. Prosser et al.

It is certified that error appears in the above-identified patent and that said Letters Patent is hereby corrected as shown below:

| Column | Line | |
|---|---|---|
| 1 | 31 | "produces" should be --produced-- |
| 3 | 40 | "refernce" should be --reference-- |
| 3 | 46, 47 | "tos cale" should be --to scale- |
| 3 | 52 | "pror" should be --prior- |
| 4 | 22 | "repsonsive" should be --responsive-- |
| 4 | 26 | "relible" should be --reliable-- |
| 4 | 52 | extend the division sign between numerator and denominator to separate "@$\lambda$1" and "@$\lambda$2" |
| 5 | 68 | "throught" should be --through-- |
| 6 | 62 | "affect" should be --effect-- |
| 7 | 25 | insert --to-- before "work" |
| 7 | 28 | insert --$\alpha$-- after "where" |
| 8 | 56, 57 | "euation" should be --equation-- |
| 9 | 32 | shift the closing parenthesis ")" down one-half line |
| 9 | 39, 40 | immediately after "$\alpha$:" on line 39, line up the expression "$\alpha = (\alpha_0)(OS) - (\alpha_D)(1-OS)$" with "(9)" on line 40 and delete "1-OS)" from line 40 |
| 9 | at 39 | beginning at this column and line and in numerous other locations in the patent, the capital letter "O" has been italicized and is easily confused with "0" (zero) |
| 12 | 22, 23 | equation (19) is included in the text rather than as a separate line and is not identified at the margin |

UNITED STATES PATENT AND TRADEMARK OFFICE
CERTIFICATE OF CORRECTION

PATENT NO. : 4,859,056

DATED : August 22, 1989

INVENTOR(S) : Stephen J. Prosser et al.

It is certified that error appears in the above-identified patent and that said Letters Patent is hereby corrected as shown below:

| | | |
|---|---|---|
| 13 | 5 | "t0" should be --$t_0$--, both occurrences |
| 13 | 10 | "β0" should be --$\beta_0$-- (three occurrences); "t0" should be --$t_0$--; italicized capital "(O)" should be --(0)-- (zero) |
| 13 | 19 | "t1" should be --$t_1$--, four occurrences; "[" (second occurrence) should be --]--; "β0 should be --$\beta_0$-- |
| 13 | 27 | "t2" should be --$t_2$-- (four occurrences); "β0" should be --$\beta_0$-- (two occurrences) |
| 13 | 33 | "t3" should be --$t_3$-- (three occurrences); "at 3" should be --$at_3$--; "β0" should be --$\beta_0$--; "α0" should be --$\alpha_0$-- |
| 14 | 30 | "β0" should be --$\beta_0$-- |
| 14 | 32 | "β0" should be --$\beta_0$--; "α0" should be --$\alpha_0$-- |
| 14 | 34 | "β0" should be --$\beta_0$-- |
| 14 | 36 | "β0" should be --$\beta_0$--; "α0" should be --$\alpha_0$-- |
| 14 | 54 | "β0" should be --$\beta_0$-- (three occurrences); "α0" should be --$\alpha_0$-- (two occurrences) |
| 15 | 1, 2 | insert a "Δ" between "k" and "l" in the numerator; insert a "Δ" immediately after the bracket ("[") in the denominator and after the second plus sign ("+") in the denominator and between "k" and "l" in the denominator; "β0" should be --$\beta_0$-- (two occurrences); "0k" should be --$_0k$ (three occurrences) |
| 15 | 41 | delete the hyphen in equation (48) where it breaks after "$\beta_0$" before the equal sign ("=") |

UNITED STATES PATENT AND TRADEMARK OFFICE
CERTIFICATE OF CORRECTION

PATENT NO. : 4,859,056
DATED : August 22, 1989
INVENTOR(S) : Stephen J. Prosser et al.

It is certified that error appears in the above-identified patent and that said Letters Patent is hereby corrected as shown below:

| | | |
|---|---|---|
| 15 | 60, 61 | delete the hyphen in equation (49) where it breaks after "$\beta_0$" before the end bracket ("]"), which should be on the first line of the equation |
| 15 | 62, 63 | delete the hyphen in equation (50) where it breaks before the second minus sign |
| 16 | 20 | the first plus sign ("+") in the numerator of equation (55) should be a minus sign (-----) |
| 16 | 30 | the superscripted "1" in the numerator of equation (56) should be the letter "l" and on the same level as the "$\alpha\Delta$" |
| 16 | 37 | the number "1" following the "$\Delta$" in the numerator of equation (57) should be the letter --l-- |
| 16 | 52 | the term "$(T_1 T_0)$" in the denominator of the dividend of equation (58) should be --$(T_1/T_0)$-- |
| 17 | 1, 3, 5, 7, 8 | in equation (59) insert a slash (--/--) between the terms "$T_1$" and "$T_0$" (four occurrences), between the terms "$T_3$" and "$T_1$" (one occurrence), and between "$T_2$" and "$T_0$" (one occurrence) |
| 17 | 3 | insert a slash (--/--) between the term "$T_3$" and "$T_0$" (only occurrence) |
| 17 | 11 | following the last equal sign in equation (59), the term "$T_1 T_0$" should be --$T_1/T_0$-- |
| 19 | 18 | "P" should be --p-- |
| 20 | 25 | "$R_{80}$" should be --$R_\lambda$-- |

UNITED STATES PATENT AND TRADEMARK OFFICE
CERTIFICATE OF CORRECTION

PATENT NO. : 4,859,056

DATED : August 22, 1989

INVENTOR(S) : Stephen J. Prosser et al.

It is certified that error appears in the above-identified patent and that said Letters Patent is hereby corrected as shown below:

| | | |
|---|---|---|
| 20 | 48 | the term to the right of the second plus sign in the denominator of equation (82) should be $--\ln(P_0(t_1)/P_0(t_0))--$ before "$]@\beta_2$" |
| 21 | 25 | "intially" should be --initially-- |
| 21 | 28 | "are" should be --after-- |
| 22 | 13 | "on" should be --of-- |
| 23 | 17 | "incude" should be --include-- |
| 26 | 10 | insert a $--\Delta--$ immediately before "tp" |
| 33 | 36 | delete "pulse", first occurrence |

Signed and Sealed this

Seventh Day of January, 1992

Attest:

HARRY F. MANBECK, JR.

*Attesting Officer*  *Commissioner of Patents and Trademarks*